United States Patent
Lu et al.

(10) Patent No.: US 11,034,689 B2
(45) Date of Patent: Jun. 15, 2021

(54) SMALL MOLECULE PROTEIN ARGININE METHYLTRANSFERASE 5 (PRMT5) INHIBITORS AND METHODS OF TREATMENT

(71) Applicant: Indiana University Research and Technology Corporation, Indianapolis, IN (US)

(72) Inventors: Tao Lu, Carmel, IN (US); Lakshmi Milind Prabhu, Indianapolis, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 0 days.

(21) Appl. No.: 16/344,644

(22) PCT Filed: Oct. 26, 2017

(86) PCT No.: PCT/US2017/058572
§ 371 (c)(1),
(2) Date: Apr. 24, 2019

(87) PCT Pub. No.: WO2018/081451
PCT Pub. Date: May 3, 2018

(65) Prior Publication Data
US 2020/0062745 A1    Feb. 27, 2020

Related U.S. Application Data

(60) Provisional application No. 62/534,969, filed on Jul. 20, 2017, provisional application No. 62/413,341, filed on Oct. 26, 2016.

(51) Int. Cl.
| | | |
|---|---|---|
| *A61P 35/00* | (2006.01) | |
| *C07D 487/04* | (2006.01) | |
| *C07D 453/02* | (2006.01) | |
| *C07C 43/23* | (2006.01) | |
| *C07D 413/14* | (2006.01) | |
| *C07D 498/22* | (2006.01) | |

(52) U.S. Cl.
CPC ............ *C07D 453/02* (2013.01); *A61P 35/00* (2018.01); *C07C 43/23* (2013.01); *C07D 413/14* (2013.01); *C07D 487/04* (2013.01); *C07D 498/22* (2013.01)

(58) Field of Classification Search
CPC .................................................. C07D 487/04
See application file for complete search history.

(56) References Cited

U.S. PATENT DOCUMENTS

| 5,064,947 A | 11/1991 | Peet |
|---|---|---|
| 6,218,387 B1 | 4/2001 | Chen |
| 2001/0000340 A1 | 4/2001 | Chen |
| 2001/0041673 A1 | 11/2001 | Fossa |

FOREIGN PATENT DOCUMENTS

| WO | 2007024680 | | 4/2001 |
|---|---|---|---|
| WO | 2007054294 | | 5/2007 |
| WO | 2012009258 | * | 1/2012 |
| WO | WO 2016/145150 | | 9/2016 |

OTHER PUBLICATIONS

STN registry search (answer 17 of 26, Registry No. 87478-95-4, Jan. 9, 2006, pp. 1-2).*
Elayne Chan-Penebre et al: "A selective inhibitor of PRMT5 with in vivo and in vitro potency in MCL models", Nature Chemical Biology, vol. 11, No. 6, Apr. 27, 2015 (Apr. 27, 2015), pp. 432-437.
Keitaro Senga et al: "Synthesis and xanthine oxidase inhibitory activity of 4,6-disubstituted 1-p-chlorophenylpyrazolo[3,4-d]pyrimidines", Journal of Heterocyclic Chemistry, vol. 19, No. 6, Nov. 1, 1982 (Nov. 1, 1982), pp. 1565-1567.
Cheng CC et al: "Potential Purine Antagonists. XII. Synthesis of 1-Alkyl(aryl)-4,6-disubstituted Pyrazolo[3,4-d]pyrimidines", Journal of Organic Chemistry, American Chemical Society, US, vol. 23, Jun. 1, 1958 (Jun. 1, 1958), pp. 852-861.
Murty Devarakonda et al: "Synthesis of novel 2-alkyl-4-substituted-amino-pyrazolo[3,4-d]pyrimidines as new leads for anti-bacterial and anti-cancer activity", Medicinal Chemistry Research., vol. 22, No. 3, Jun. 4, 2012 (Jun. 4, 2012), pp. 1090-1101.
Gui-Mei Kong et al: Selective small-chemical inhibitors of protein arginine methyltransferase 5 with anti-lung cancer activity, PLOS ONE, vol . 12, No. 8, Aug. 14, 2017 (Aug. 14, 2017), pp. 1-23.
International Search Report and Written Opinion dated Feb. 22, 2018 in counterpart International Application No. PCT/US2017/058572.
Miyashita et al., Studies on Pyrazolo[3,4-d]pyrimidine Derivatives. XVII. Reactions of 5-Benzoyl-4,5-dihydro-6-methyl-1-phenyl-1H-pyrazolo[3,4-d]pyrimidine-4-carbonitrile (The 6-Methylprazolopyrimidine Reissert Compound), Chemical and Pharmaceutical Bulletin, 1990, vol. 38, pp. 230-233; p. 231.

* cited by examiner

*Primary Examiner* — Susanna Moore
(74) *Attorney, Agent, or Firm* — Barnes & Thornburg LLP

(57) ABSTRACT

Provided are compounds of formulas (I), (II), (III), and (IV), which effectively inhibit protein arginine methyltransferase 5 (PRMT5). Also provided are methods of using the compounds, including a method of treating cancer, a method of inhibiting the activity of PRMT5 in a cell, and a method of treating a disease associated with increased activity of PRMT5.

7 Claims, 28 Drawing Sheets

Figure 1:
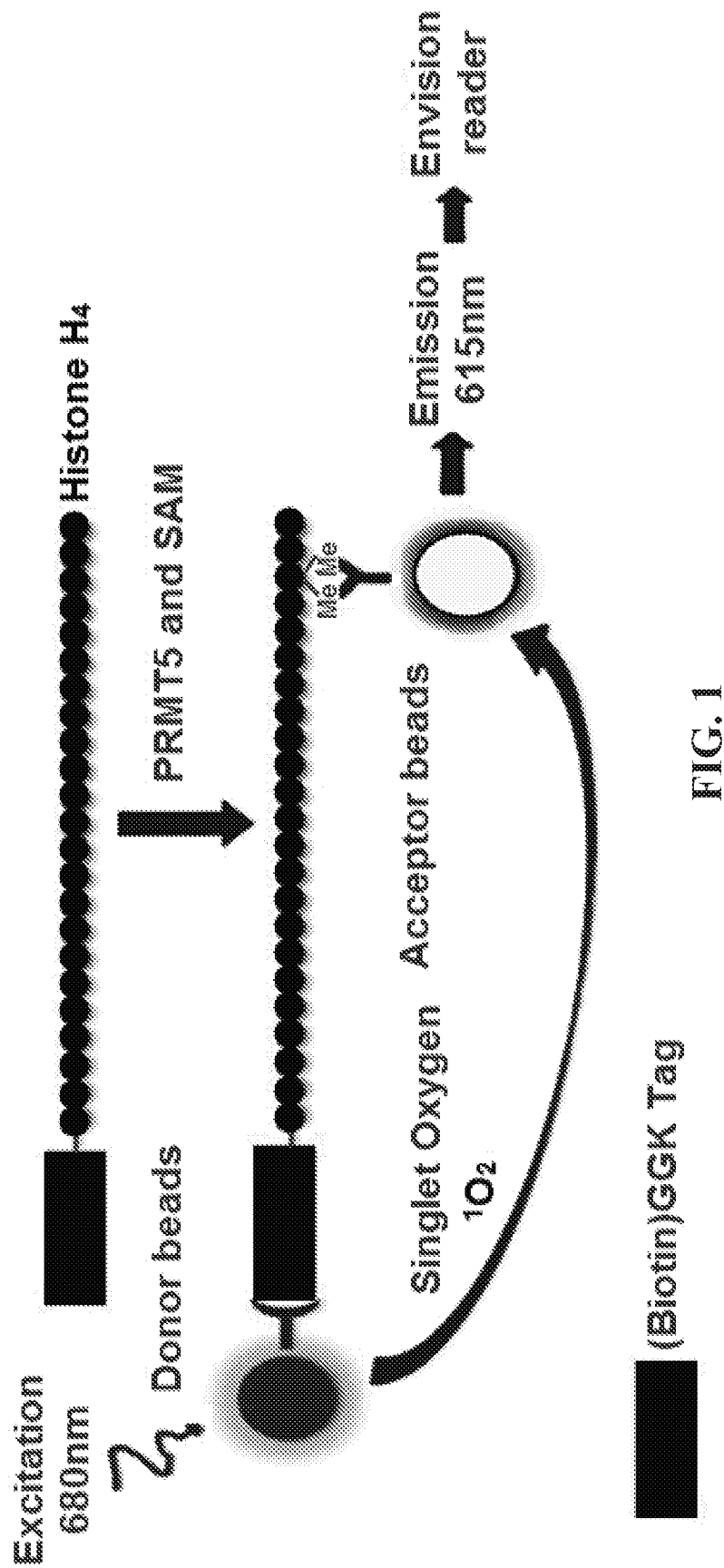

| | Derivative Name | HT-29 IC$_{50}$ (µM) |
|---|---|---|
| | Parental: Compound (IIa) | 10 |
| 1 | (Ia) | 2 |
| 2 | (If) | 7 |
| 3 | (Ig) | 7 |

FIG. 3A

| | Derivative Name | PANC1 IC$_{50}$ (µM) |
|---|---|---|
| | Parental: Compound (IIa) | 4 |
| 1 | (Ia) | 2 |
| 2 | (If) | 8 |
| 3 | (Ig) | 11 |
| 4 | (Ib) | 11 |

FIG. 3B

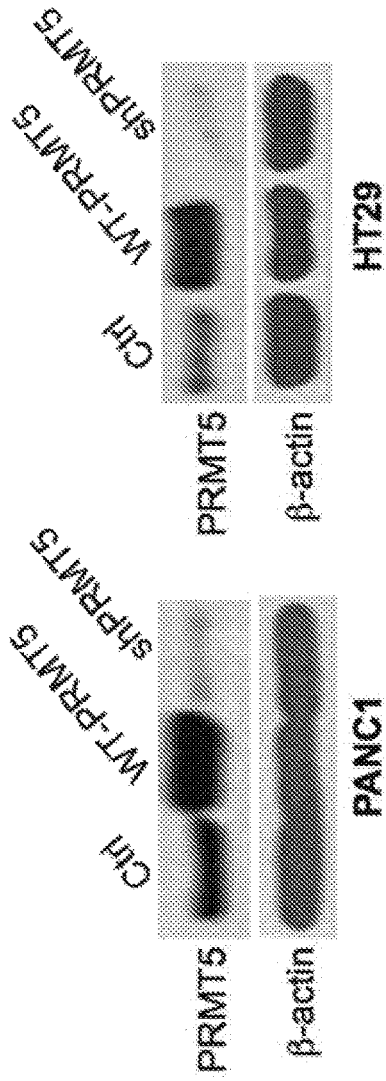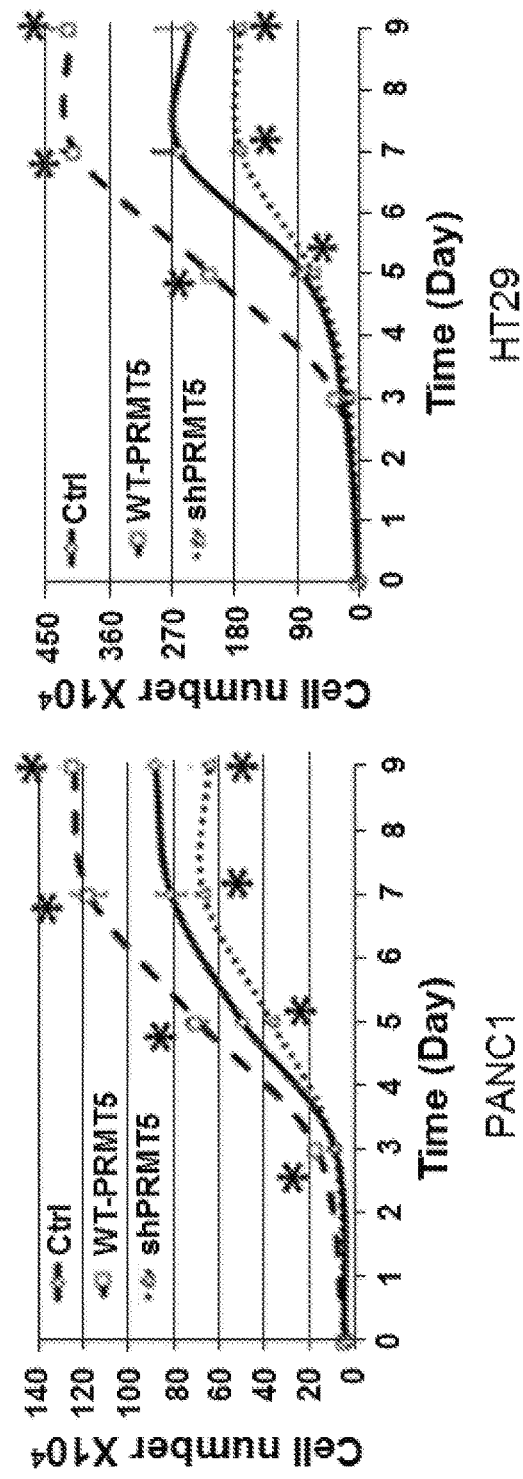
FIG. 5A
FIG. 5B
FIG. 5C

| Cancer Type | Cell Line | Compound (Ia) IC$_{50}$, µM |
|---|---|---|
| PDAC | PANC1 | 4.3 |
| CRC | HT29 | 2.2 |

FIG. 6C

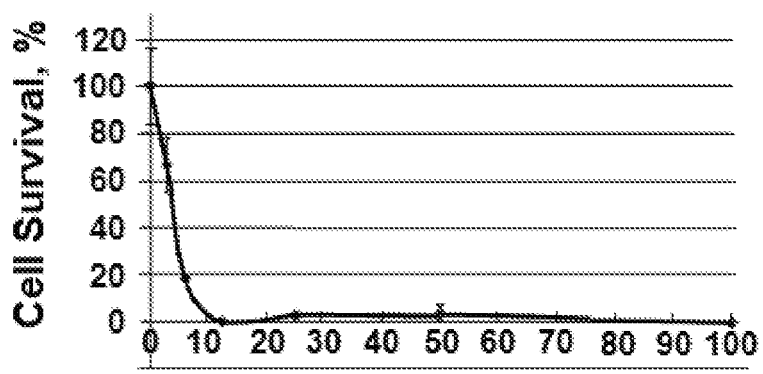
FIG. 8A  Compound (IIa), μM  PANC1
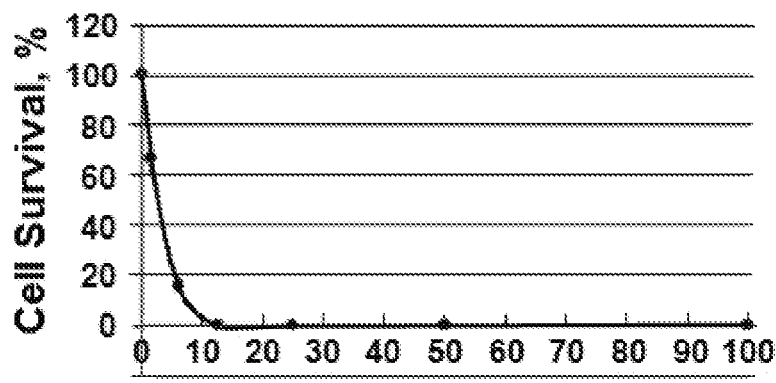
FIG. 8B  Compound (IIa), μM  MiaPaCa2
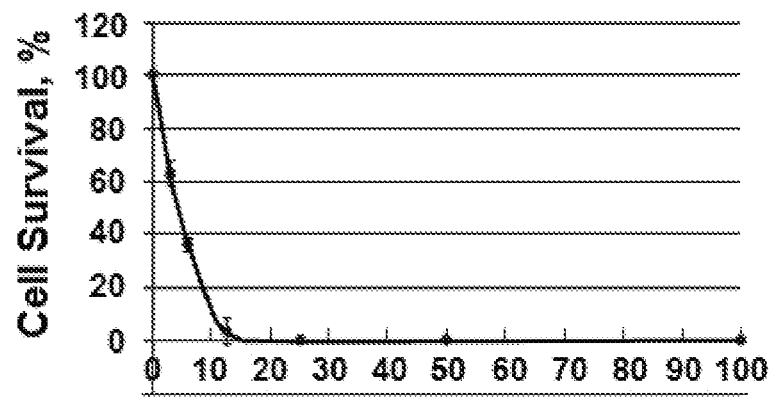
FIG. 8C  Compound (IIa), μM  AsPC1

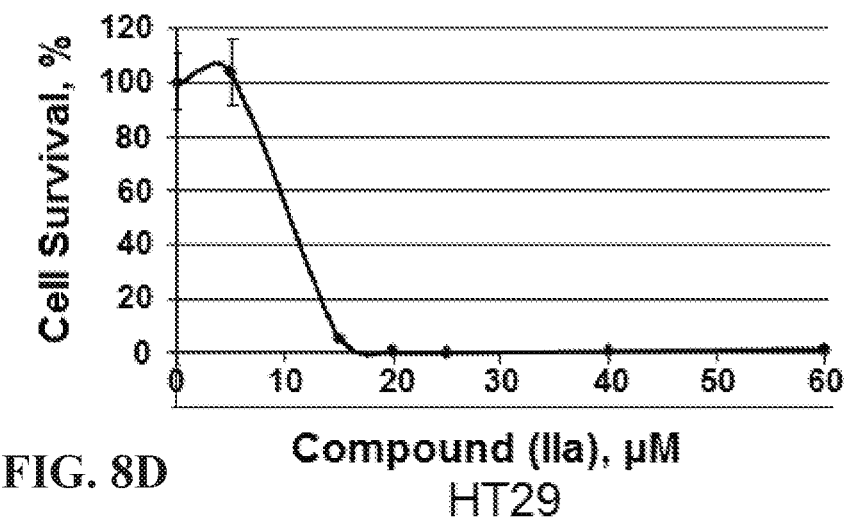
FIG. 8D HT29
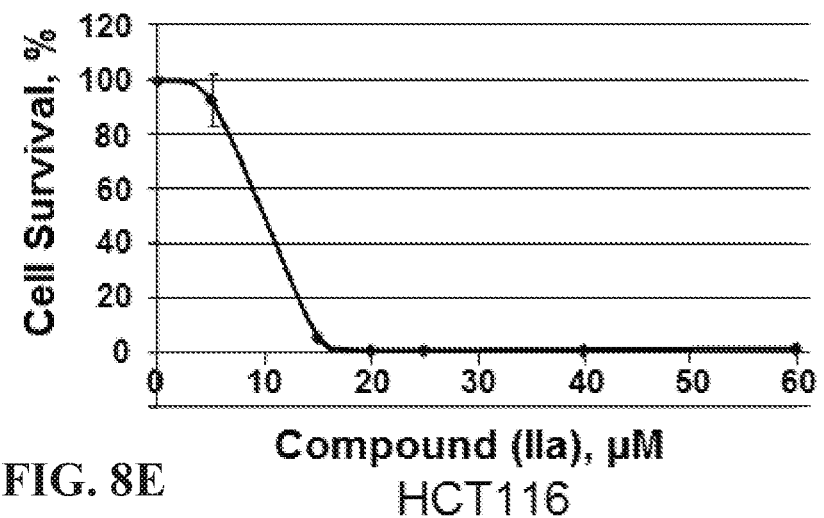
FIG. 8E HCT116
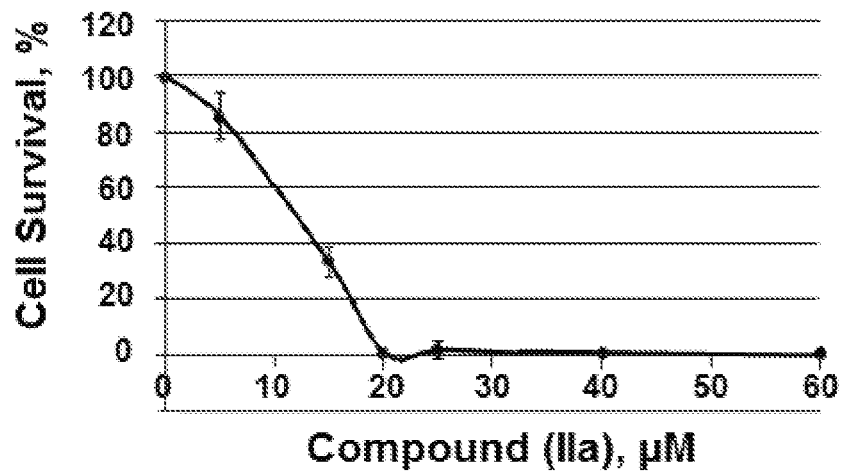
FIG. 8F DLD1

| Cancer Type | Cell line | IC50, µM |
|---|---|---|
| PDAC | PANC1 | 4 |
| | MiaPaCa2 | 2 |
| | AsPC1 | 4 |
| CRC | HT29 | 10 |
| | HCT116 | 10 |
| | DLD1 | 11 |

PANC1

MiaPaCa2

AsPC1

| Cancer Type | Cell line | IC50, µM |
|---|---|---|
| PDAC | PANC1 | 95 |
| | MiaPaCa2 | 62 |
| | AsPC1 | 50 |
| CRC | HT29 | 190 |
| | HCT116 | 180 |
| | DLD1 | 195 |

FIG. 9G

TNFα, PANC1

IL8, PANC1

TNFα, HT29

IL8, HT29

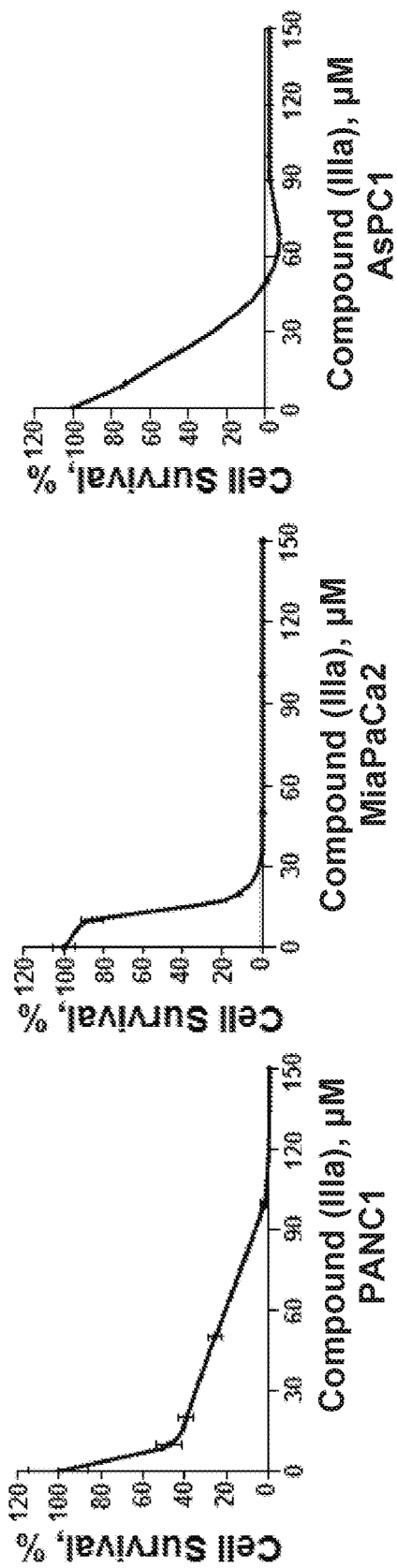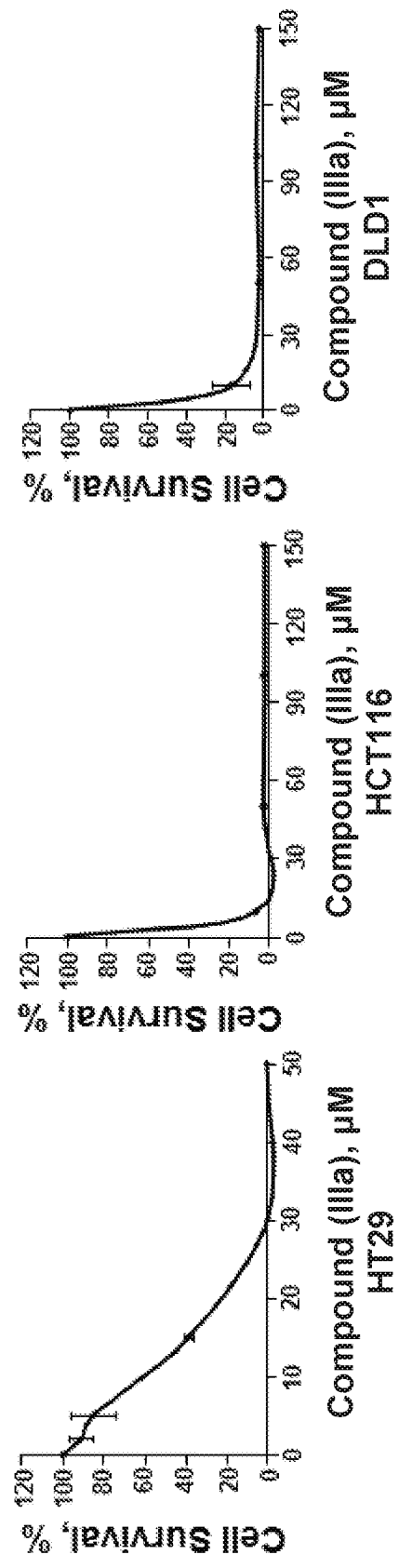
FIG. 12A PANC1
FIG. 12B MiaPaCa2
FIG. 12C AsPC1
FIG. 12D HT29
FIG. 12E HCT116
FIG. 12F DLD1

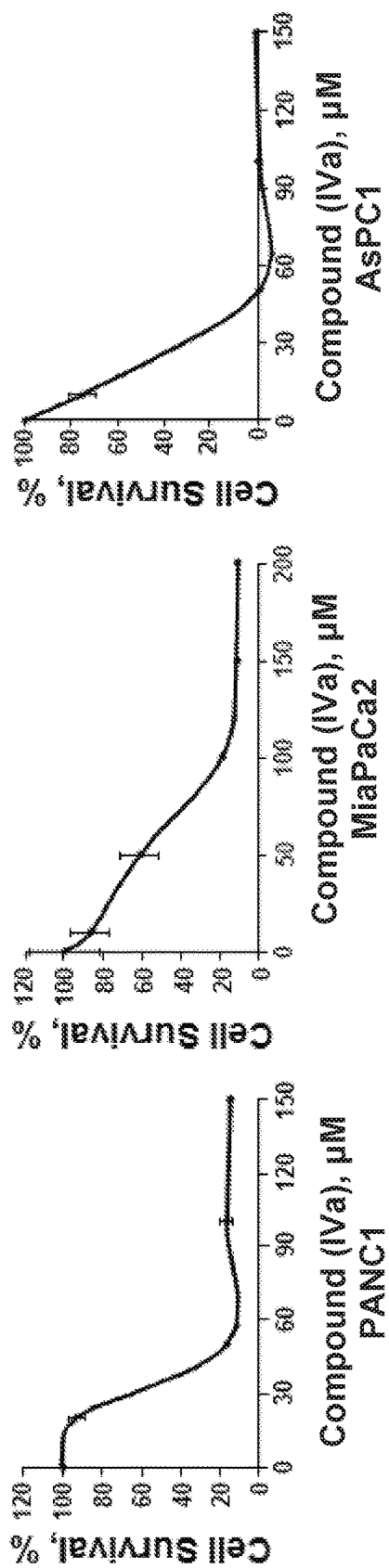
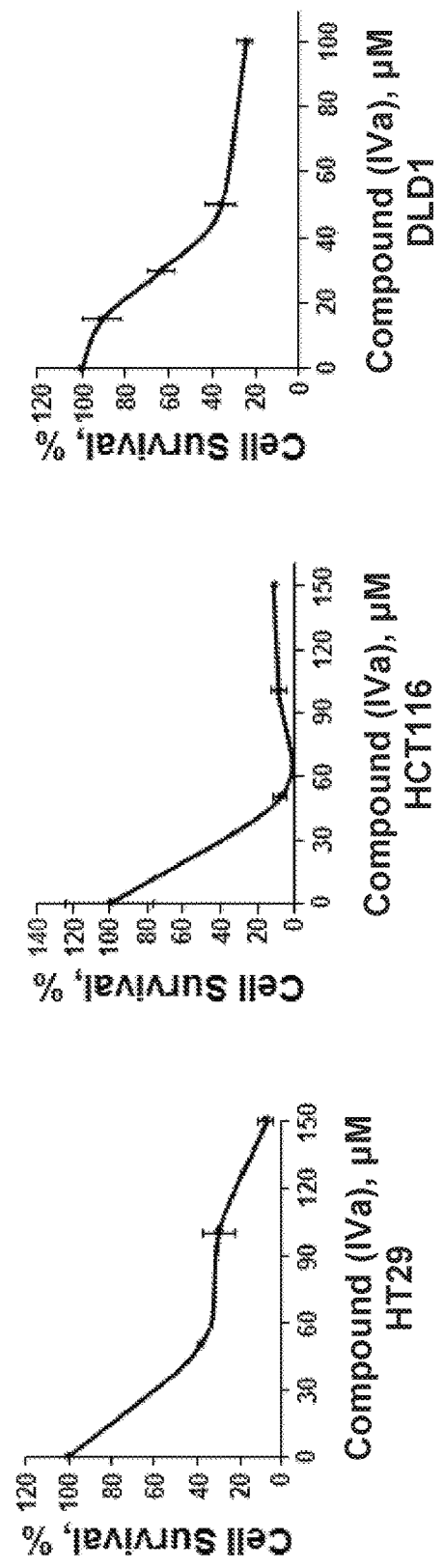
FIG. 12G  FIG. 12H  FIG. 12I
FIG. 12J  FIG. 12K  FIG. 12L

| Cancer Type | Cell Line | Compound (IIIa) IC$_{50}$, µM | Compound (IVa) IC$_{50}$, µM |
|---|---|---|---|
| PDAC | PANC1 | 8.5 | 34 |
| | MiaPaCa2 | 12.5 | 51 |
| | AsPC1 | 11 | 22 |
| CRC | HT29 | 11 | 50 |
| | HCT116 | 5 | 35 |
| | DLD1 | 5 | 38 |

FIG. 12M

SMALL MOLECULE PROTEIN ARGININE METHYLTRANSFERASE 5 (PRMT5) INHIBITORS AND METHODS OF TREATMENT

CROSS-REFERENCE TO RELATED APPLICATIONS

This patent application is a 35 U.S.C. § 371 national phase application of International Application Serial No. PCT/US2017/058572, filed Oct. 26, 2017, which claims the benefit of U.S. Provisional Patent Application No. 62/413,341, filed Oct. 26, 2016, and U.S. Provisional Patent Application No. 62/534,969, filed Jul. 20, 2017, both of which are incorporated in their entirety by reference.

STATEMENT REGARDING FEDERALLY SPONSORED RESEARCH AND DEVELOPMENT

This invention was made with Government support under Grant Number TR001108 awarded by the National Institutes of Health. The Government has certain rights in the invention.

BACKGROUND OF THE INVENTION

Posttranslational modifications (PTMs) regulate protein function in eukaryotes and have been shown to play a role in a variety of cellular functions. In the past decade, research has greatly advanced the understanding of the role of PTMs of various signaling molecules that lead to the development of a variety of diseases, including cancers (Karve et al., *J. Amino Acids*, 2011; 2011: 207691). Methylation of lysine and arginine is one of the most critical PTMs seen in nature and is implicated in a number of cellular processes, such as DNA damage and repair, gene transcription and translation, and protein subcellular localization and translocation. Arginine methylation is carried out by a group of enzymes termed protein arginine methyltransferases. Amongst this family, protein arginine methyltransferase 5 (PRMT5) has been implicated in the development of a wide range of diseases. For example, the expression of PRMT5 is upregulated in a variety of cancers (e.g., liver cancer, pancreatic cancer, breast cancer, prostate cancer, and lung cancer, as well as lymphoma and melanoma), neurodegenerative disorders, inflammatory diseases, metabolic disorders, cardiovascular diseases, autoimmune disorders, and blood disorders.

PRMT5 is an activator of NF-κB via dimethylating arginine 30 of the p65 subunit of NF-κB. NF-κB is a critical eukaryotic transcription factor whose family consists of five members: RelA (p65), RelB, cRel, NF-κB1 (p50 and its precursor p105), and NF-κB2 (p52 and its precursor p100) (Ghosh et al., *Annu Rev Immunol*, 1998; 16: 225-260). NF-κB signaling can be classified into canonical and non-canonical pathways. The canonical pathway has been well established as a key contributor to development of both pancreatic ductal adenocarcinoma (PDAC) (Prabhu et al., *Oncotarget*, 2014; 5: 10969-10975; Liou et al., *J Cell Biol*, 2013; 202: 563-577) and colorectal cancer (CRC) (Agarwal et al., *Oncogene*, 2005; 24(6): 1021-31; Yu et al., *Int J Colorectal Dis*, 2004; 19: 18-22). In this pathway, inhibitor of κB (IκBα) sequesters the p65:p50 heterodimer in an inactive state in the cytoplasm. When a cell receives extracellular signals, such as stress or pro-inflammatory cytokines, IκB kinase phosphorylates IκBα, which leads to the degradation of IκB and release of the p65:p50 complex and the activation of NF-κB target genes (Gilmore, *Oncogene*, 2006; 25: 6680-6684). A number of these downstream NF-κB target genes have been implicated in a wide range of diseases including cancer, neurodegenerative disorders, inflammatory diseases, metabolic disorders, cardiovascular diseases, autoimmune disorders, and blood disorders. Increased NF-κB activation is shown to be associated with a poor disease prognosis, and linked to developing resistance against chemotherapy (Arora et al., *J Biol Chem*, 2013; 288: 21197-207; Lind et al., *Surgery*, 2001; 130: 363-69).

Accordingly, there is a need to identify new compounds for the treatment of PRMT5-associated diseases. This invention provides such compounds and associated methods.

BRIEF SUMMARY OF THE INVENTION

The invention provides compounds of formula (I), formula (II), formula (III), and formula (IV)

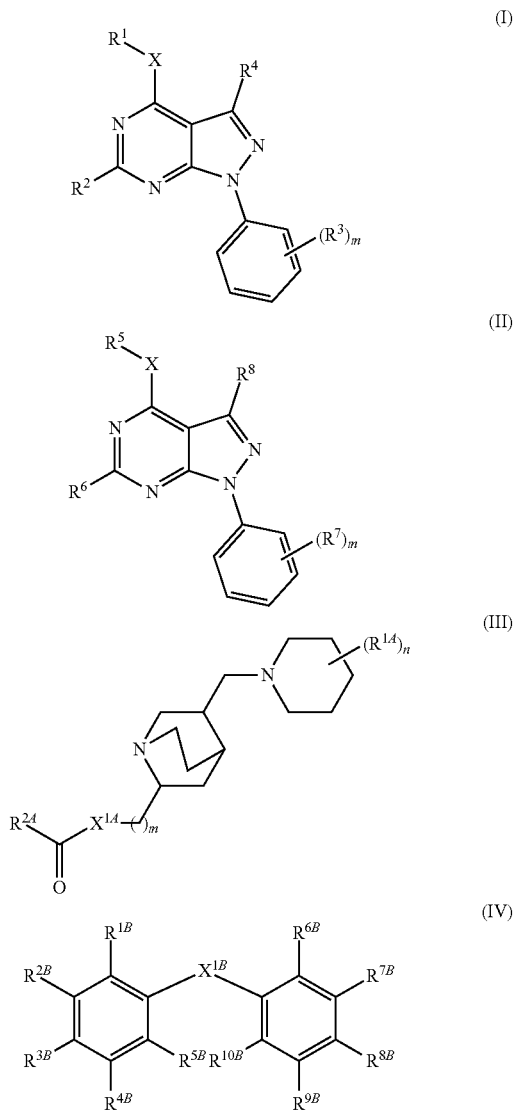

in which $R^1$, $R^2$, $R^3$, $R^4$, $R^5$, $R^6$, $R^7$, $R^8$, $R^{1A}$, $R^{2A}$, $R^{2B}$, $R^{3B}$, $R^{4B}$, $R^{5B}$, $R^{6B}$, $R^{7B}$, $R^{8B}$, $R^{9B}$, $R^{10B}$, X, $X^{1A}$, $X^{1B}$, m, and n are described herein. It has been discovered that compounds defined by formula (I), formula (II), formula (III), or formula (IV) are effective in inhibiting PRMT5, thereby making the compounds effective in treating diseases associated with increased expression or activity of PRMT5 (e.g., cancer).

The invention further provides a method of treating a cancer in a subject comprising administering a pharmaceutically effective amount of a compound of formula (I), formula (II), formula (III), or formula (IV), or a pharmaceutically acceptable salt thereof to the subject.

Also provided is a method of inhibiting the activity of PRMT5 in a cell comprising administering a pharmaceutically effective amount of a compound of formula (I), formula (II), formula (III), or formula (IV), or a pharmaceutically acceptable salt thereof to the cell.

The invention also provides a method of treating a disease associated with increased expression or activity of PRMT5 in a subject comprising administering a pharmaceutically effective amount of a compound of formula (I), formula (II), formula (III), or formula (IV), or a pharmaceutically acceptable salt thereof to the subject.

BRIEF DESCRIPTION OF THE SEVERAL VIEWS OF THE DRAWING(S)

FIG. 1 is a schematic illustration of the AlphaLISA technique for the identification of small-molecule PRMT5 inhibitors. Biotinylated substrate (histone H4) is incubated with PRMT5 and methyl donor, S-adenosyl-1-methionine (SAM). PRMT5 symmetrically dimethylates the third arginine (R3) on biotin-H4 to form biotin-H4R3me2. This product is recognized by Acceptor beads specific for this methylation site. Donor beads have a streptavidin tag and bind to biotin-H4. Interaction between the Acceptor and Donor beads emits a chemiluminescent signal, which is detected by an ENVISION™ Reader (PerkinElmer, Waltham, Mass.). The methylation activity of PRMT5 is proportional to the intensity of this signal.

Figure 2A:
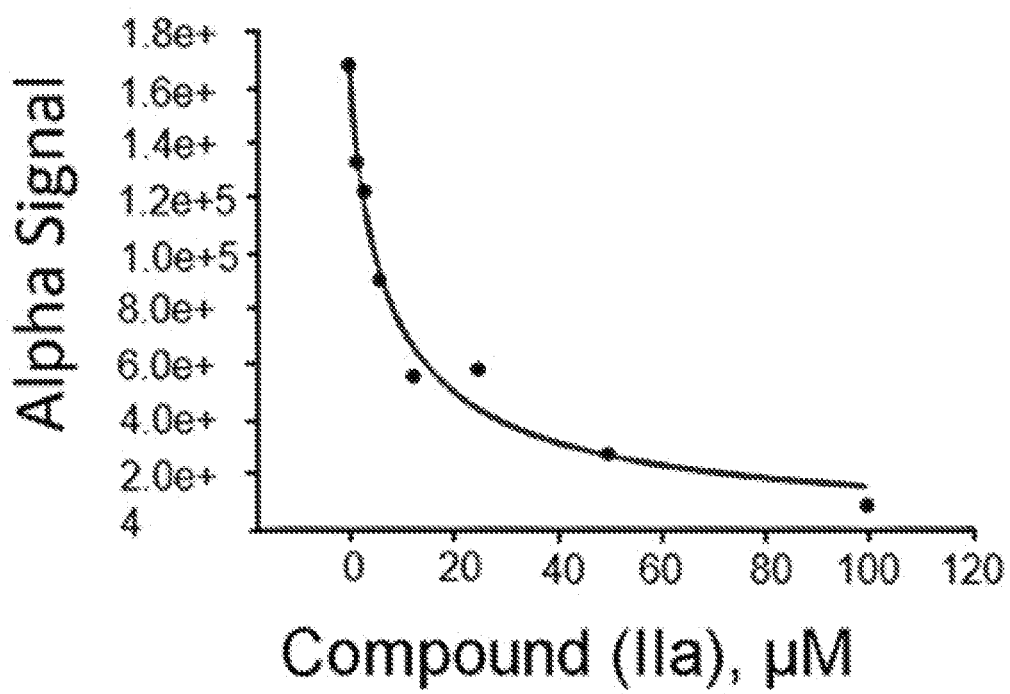
Figure 2B:
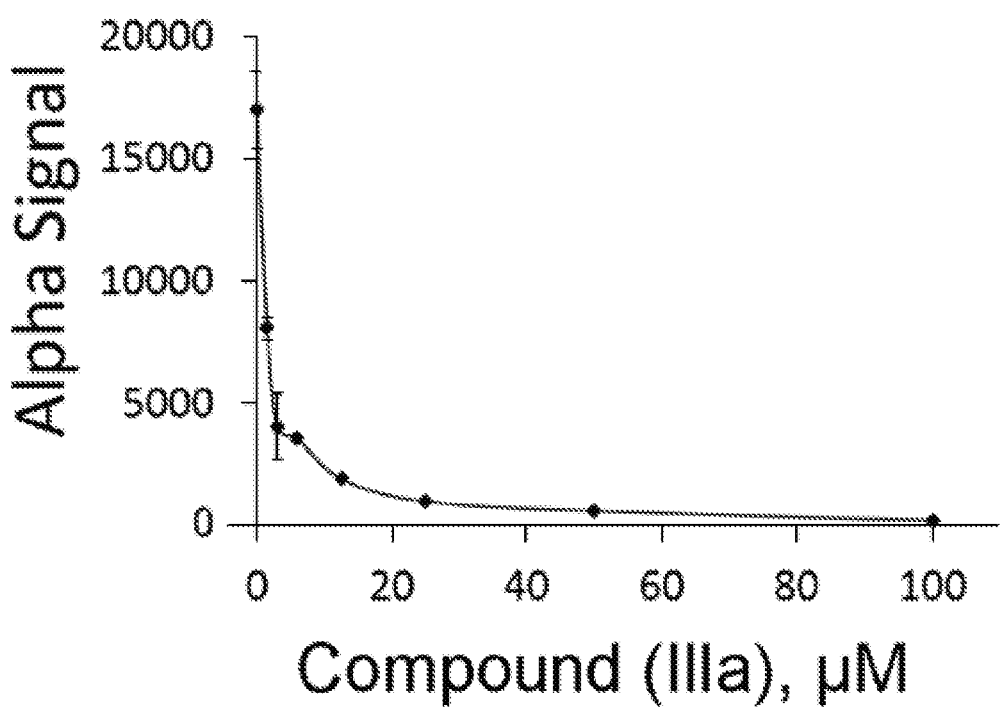
Figure 2C:
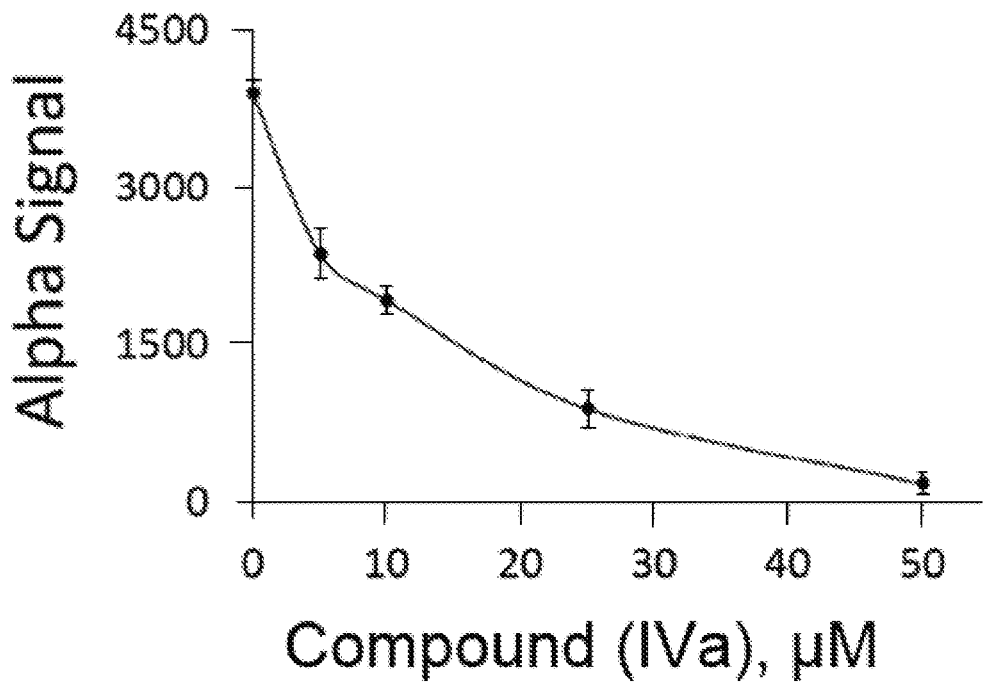
Figure 2D:
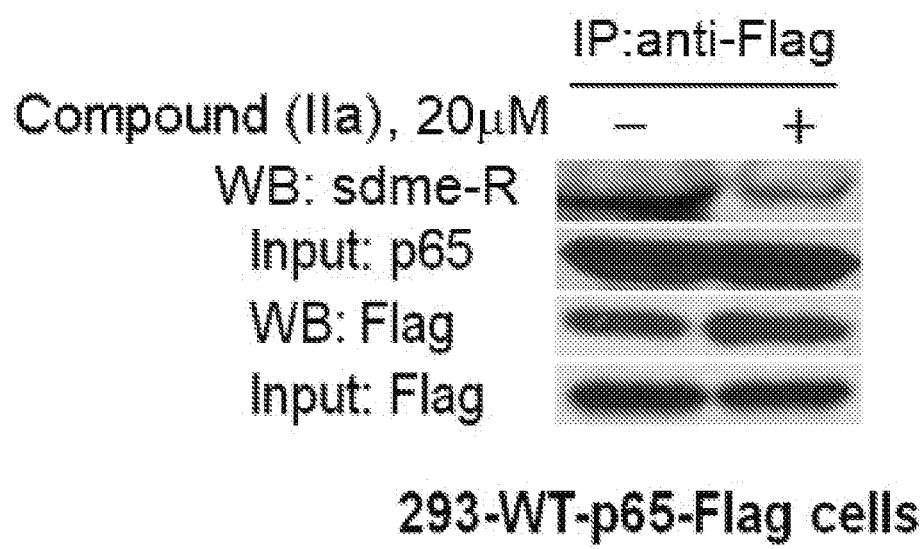

FIGS. 2A-D depict the experimental results of studies to determine the PRMT5 inhibitory activity of a compound of formula (II), a compound of formula (III), and a compound of formula (IV). FIG. 2A is a calculation of $IC_{50}$ of compound (IIa) using AlphaLISA, which was found to be ~7.5 μM. FIG. 2B is a calculation of $IC_{50}$ of compound (IIIa) using AlphaLISA, which was found to be ~1.5 μM. FIG. 2C is a calculation of $IC_{50}$ of compound (IVa) using AlphaLISA, which was found to be ~16.5 μM. FIG. 2D is a co-immunoprecipitation-Western blot, showing that treatment with 20 μM compound (IIa) for 24 hours inhibited the methylation of PRMT5 substrate, p65, in 293-WT-p65-Flag cell lines. Flag beads were used to pull down WT-p65-Flag and samples were then probed with anti-symmetric dimethyl arginine motif Ab (sdme-RG Ab) to detect dimethylation levels of the p65 subunit.

FIGS. 3A-B depict the results of lead optimization studies to identify PRMT5 inhibitors. FIG. 3A is a table showing the calculation of $IC_{50}$ of compounds (Ia), (If), and (Ig) compared to the parent compound (IIa) in HT-29 colon cancer cells. FIG. 3B is a table showing the calculation of $IC_{50}$ of compounds (Ia), (Ib), (If), and (Ig) compared to the parent compound (IIa) in PANC1 pancreatic cancer cells.

Figure 4A:
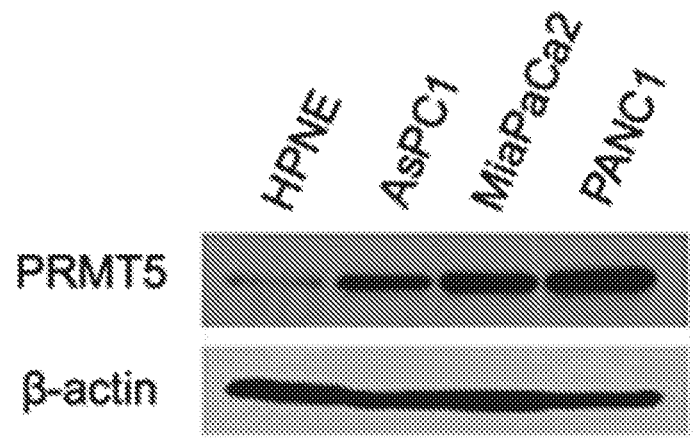
Figure 4B:
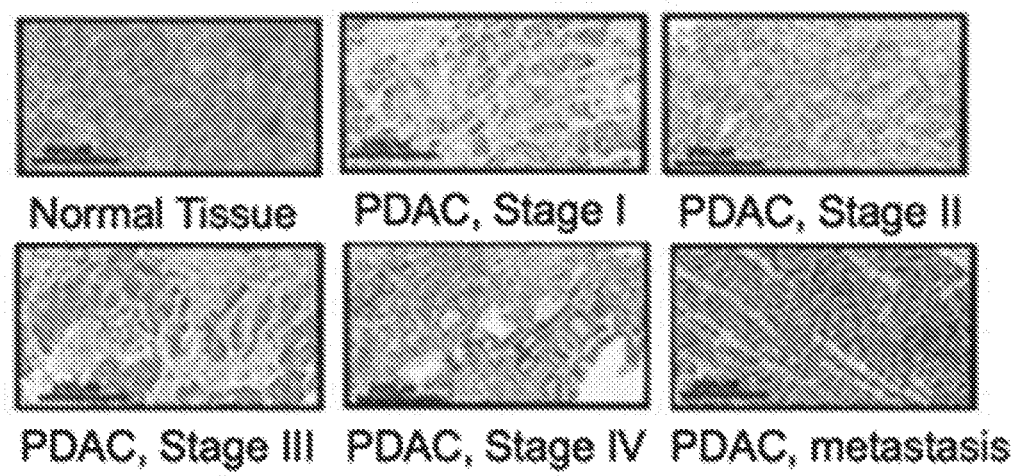
Figure 4C:
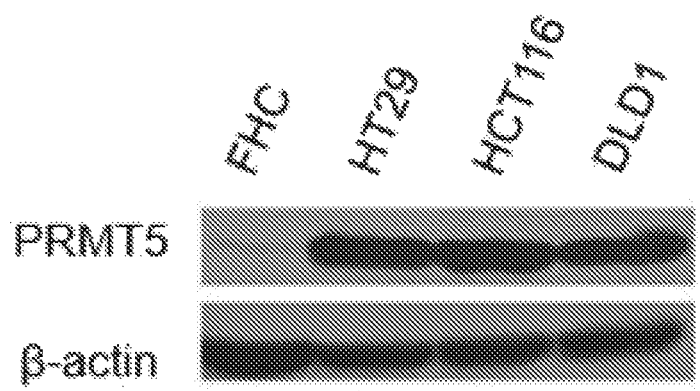
Figure 4D:
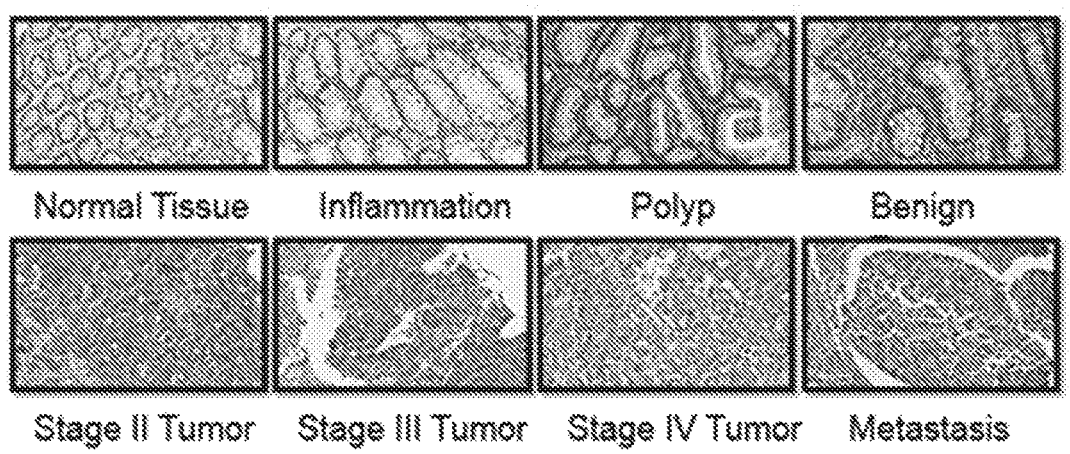

FIGS. 4A-D depict the experimental results of studies to determine the expression level of PRMT5 in multiple cancer types. FIG. 4A is a Western blot showing that PRMT5 protein expression is higher in PDAC cell lines, AsPC1, MiaPaCa2 and PANC1, as compared to a control pancreatic cell line, HPNE. β-actin was used as a loading control. FIG. 4B is immunohistochemical (IHC) staining demonstrating that PRMT5 protein expression is higher in PDAC tumor tissue as compared to the tissue from normal (i.e., non-cancerous) controls. FIG. 4C is a Western blot showing that PRMT5 protein expression is higher in CRC cell lines, HT29, HCT116 and DLD1, as compared to a control colon cell line, FHC. β-Actin was used as a loading control. FIG. 4D is IHC staining showing that PRMT5 protein expression was higher in the polyp stage and advanced stages of CRC, including stages II, III, IV, and the metastatic stage, compared to normal, non-cancerous colon tissue.

Figure 5D:
Figure 5D:
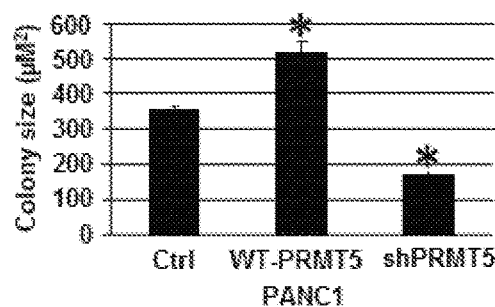
Figure 5D:
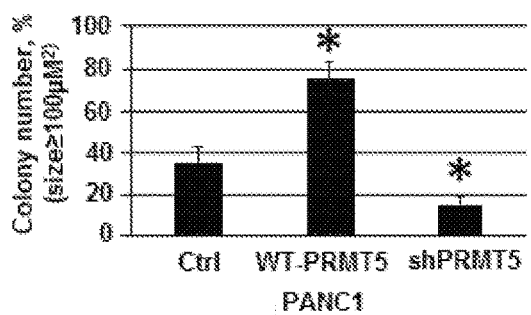
Figure 5E:
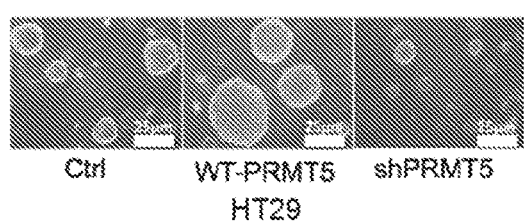
Figure 5E:
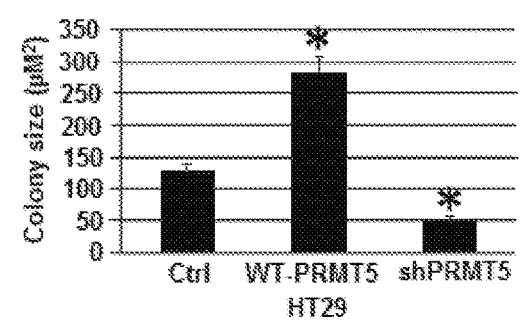
Figure 5E:
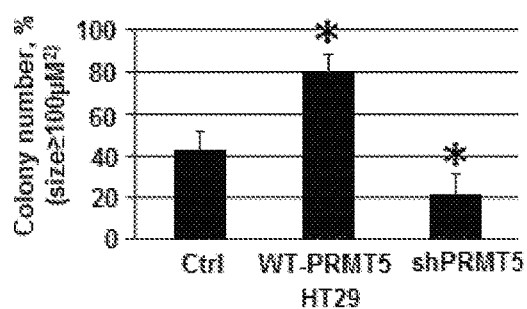
Figure 5F:
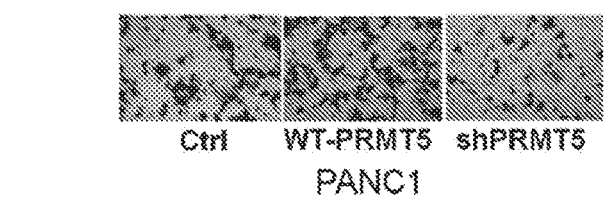
Figure 5F:
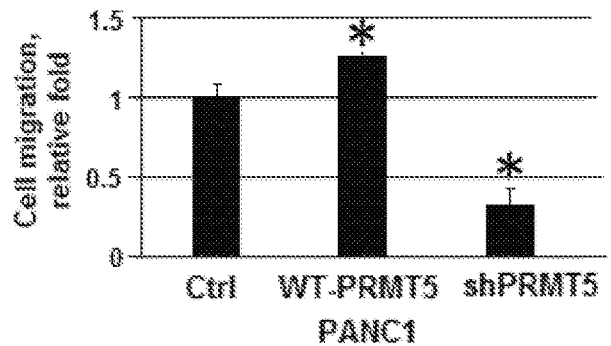
Figure 5G:
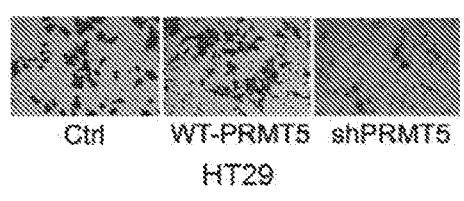
Figure 5G:
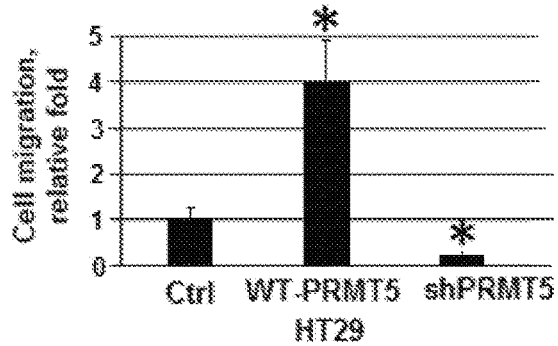

FIGS. 5A-G depict the experimental results of studies to determine the effect of increased PRMT5 activity in cells. FIG. 5A is Western blot, confirming stable PRMT5 overexpression and shPRMT5 knockdown in PANC1 (left panel) and HT29 (right panel) cell lines. β-Actin was used as a loading control. FIGS. 5B and 5C are a cell proliferation assay, showing the effect of PRMT5 overexpression and shPRMT5 knockdown on cell growth in PANC1 (FIG. 5B) and HT29 (FIG. 5C) cell lines. Cell proliferation was significantly higher in the WT-PRMT5 cell lines, while shPRMT5 cells showed the opposite effect in both PANC1 and HT29 cell lines. FIGS. 5D and 5E are an anchorage-independent assay, showing the effect of PRMT5 overexpression and shPRMT5 knockdown on the colony size and colony number in PANC1 (FIG. 5D) and HT29 (FIG. 5E) cells. Anchorage-independent growth was significantly higher in the WT-PRMT5 cell lines, while significantly reduced in the shPRMT5 cells. FIGS. 5F and 5G are a cell migration assay, showing the effect of PRMT5 overexpression and shPRMT5 knockdown on cell migration in PANC1 (FIG. 5F) and HT29 (FIG. 5G) cell lines. The upper panels show representative pictures of the respective wells with 20× magnification. The lower panel denotes the quantification for the change in migration between the cell lines. Cell migration was significantly higher in the WT-PRMT5 overexpression cells, while significantly reduced in the shPRMT5 cells. The data represent the means±SD for three independent experiments. *P<0.05 vs. Ctrl group.

Figure 6A:
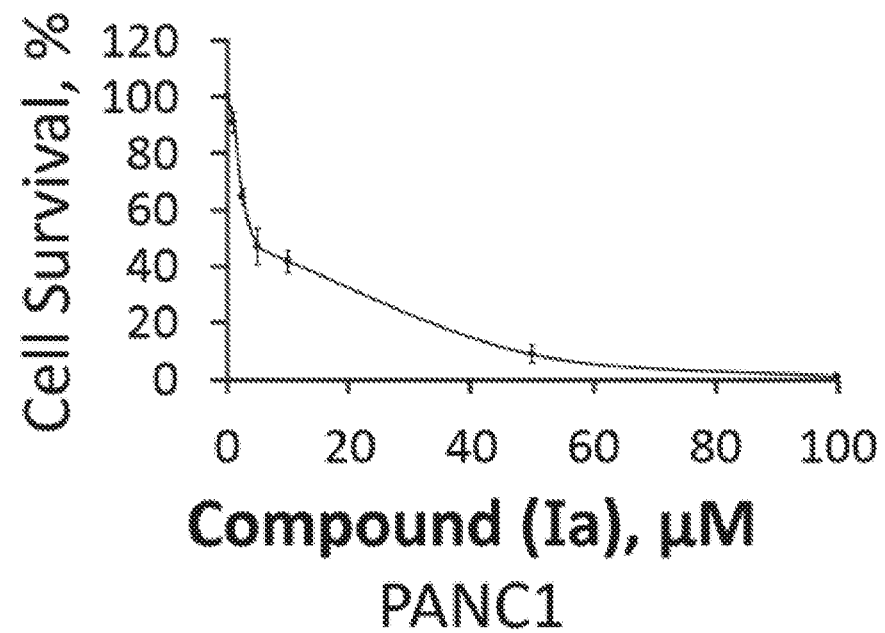
Figure 6B:
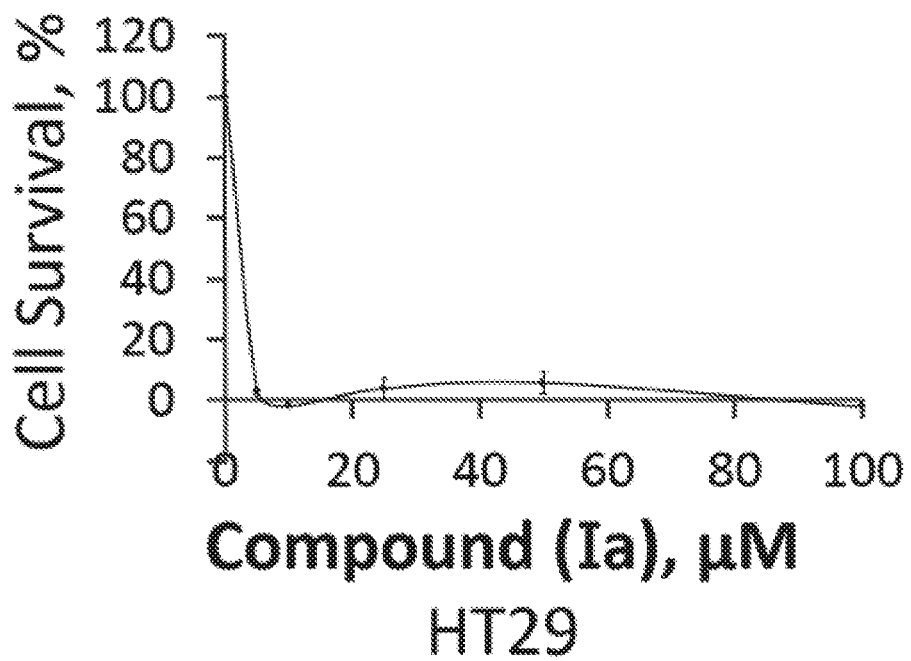

FIGS. 6A-C depict the results of experiments to determine the inhibitory effect of compound (Ia) in multiple cancer types. FIG. 6A is an MTT assay in PDAC cells (PANC1), demonstrating that cell viability decreased significantly in the presence of increasing concentrations of compound (Ia). FIG. 6B is an MTT assay in CRC cells (HT29), showing that cell viability decreased significantly in the presence of increased concentrations of compound (Ia). FIG. 6C is a table, summarizing the $IC_{50}$ values for compound (Ia) in PDAC and CRC cells, respectively.

Figure 7A:
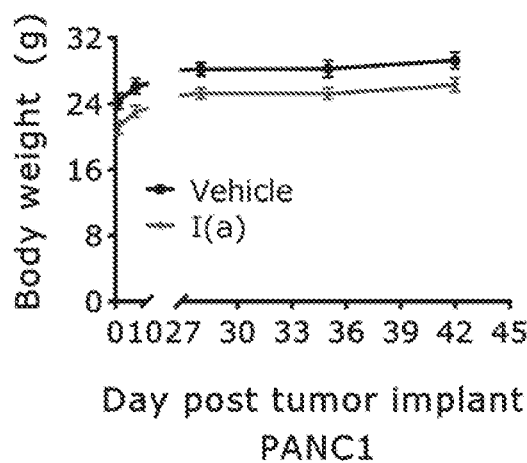
Figure 7B:
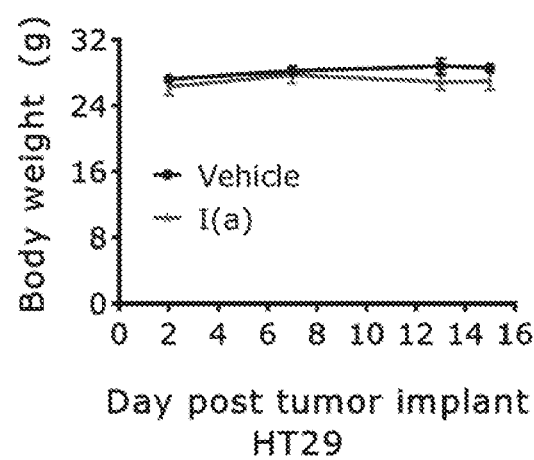
Figure 7C:
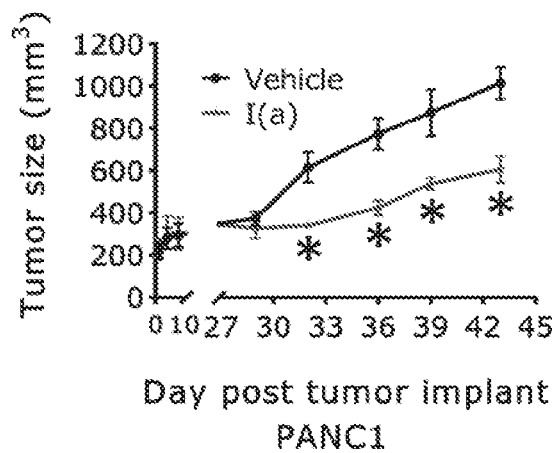
Figure 7D:
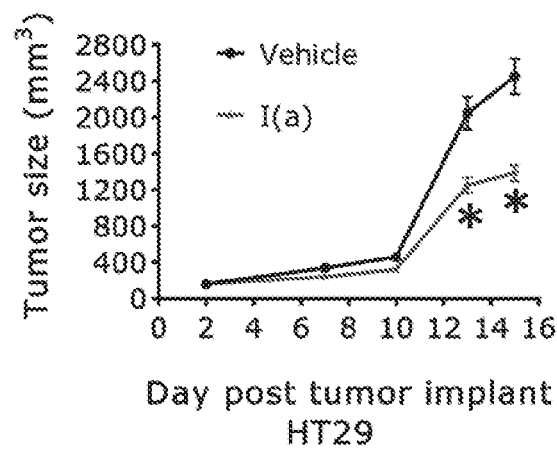

FIGS. 7A-D depict the results of experiments to determine the in vivo effect of compound (Ia). FIGS. 7A and 7B show that no significant changes in body weight were observed over the course of treatment in either PANC1 (FIG. 7A) or HT29 (FIG. 7B) model after treatment with 20 mg/kg of compound (Ia). (*P<0.05, n=4). FIGS. 7C and 7D are a tumor efficacy study, in which PANC1 (FIG. 7C) or HT29 (FIG. 7D) cells were subcutaneously implanted in NSG mice. Tumor volumes were measured and inhibition of tumor growth was observed upon treatment with 20 mg/kg of compound (Ia) intraperitoneally for 3×/week, as compared to the vehicle control. (*P<0.05, n=4).

Figures 8G, 8H:
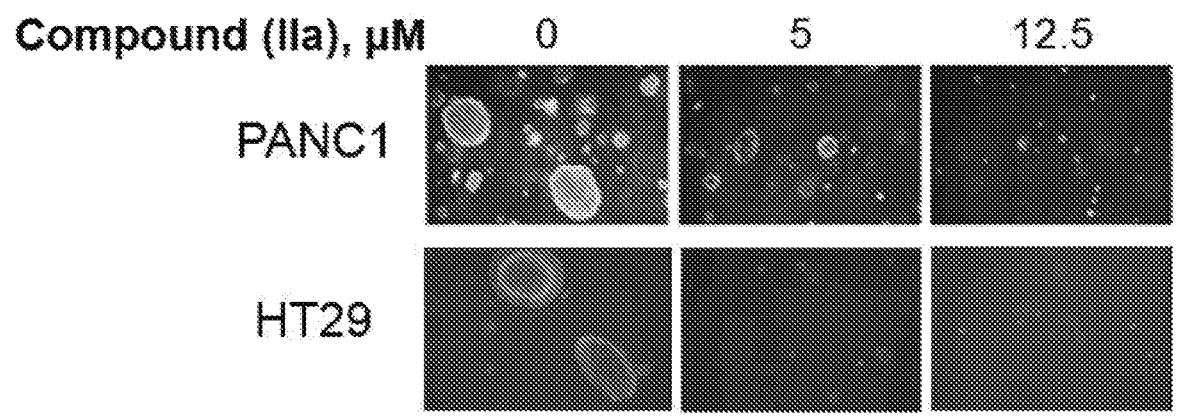

FIGS. 8A-H depict the results of experiments to determine the inhibitory effect of compound (IIa) in multiple cancer types. FIGS. 8A-C are an MTT assay in PDAC cells (PANC1, MiaPaCa2, and AsPC1), demonstrating that cell viability decreased significantly in the presence of increasing concentrations of compound (IIa). FIGS. 8D-F are an MTT assay in CRC cells (HT29, HCT116, and DLD1), showing that cell viability decreased significantly in the presence of increased concentrations of compound (IIa). FIG. 8G is a table, summarizing the $IC_{50}$ values for compound (IIa) in PDAC and CRC cells, respectively. FIG. 8H is an anchorage-independent assay, showing that with increasing concentrations of compound (IIa), there was a significant decrease in the anchorage-independent growth ability in both PANC1 as well as HT29 cells.

Figure 9A:
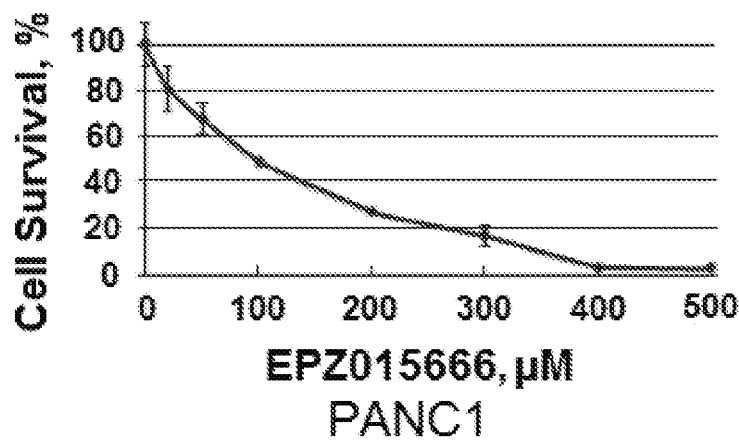
Figure 9B:
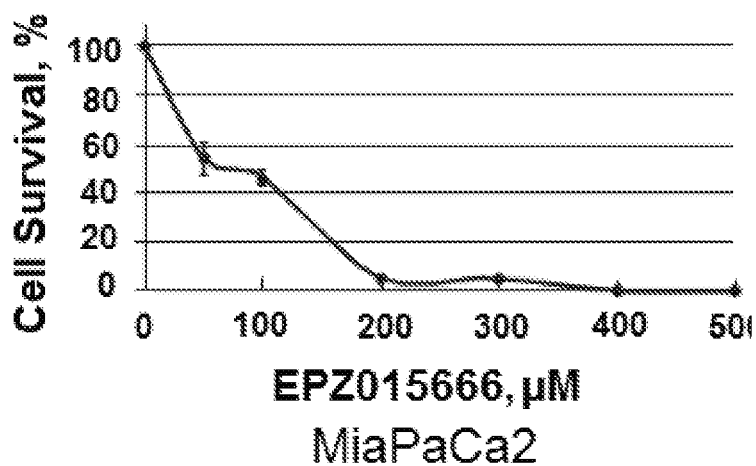
Figure 9C:
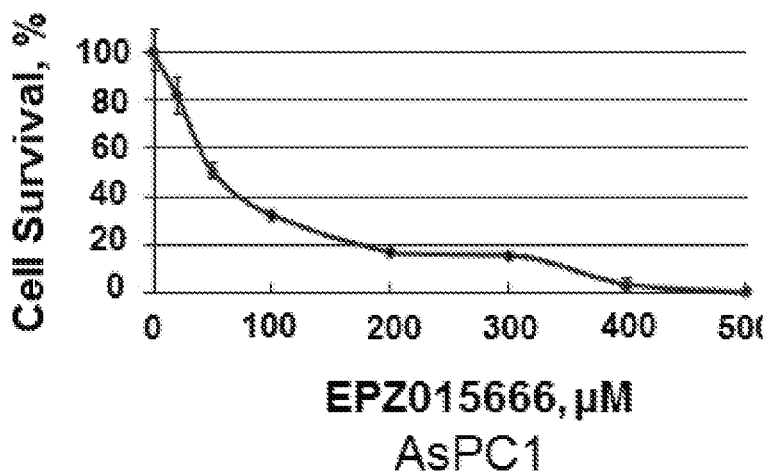
Figure 9D:
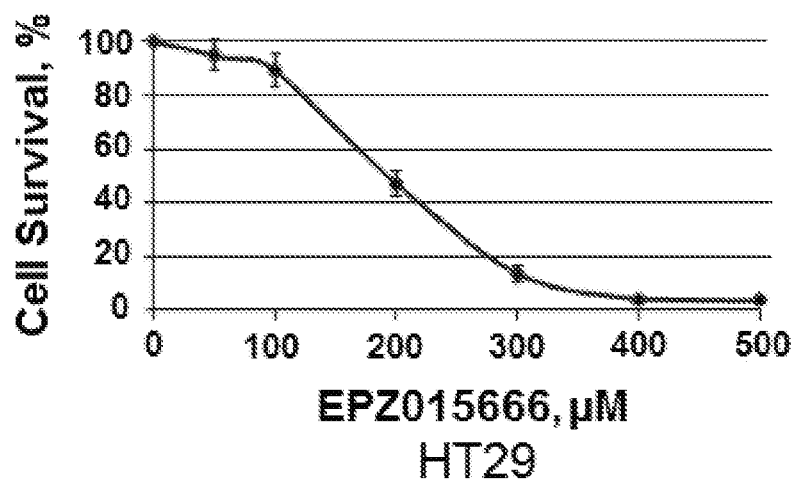
Figure 9E:
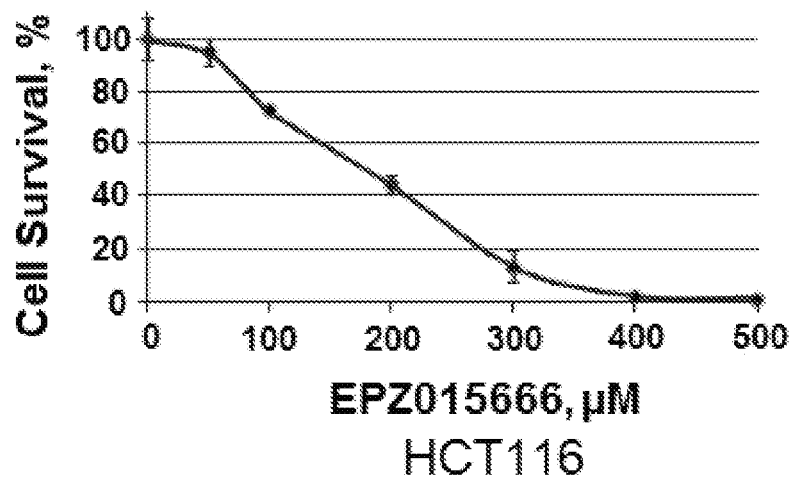
Figure 9F:
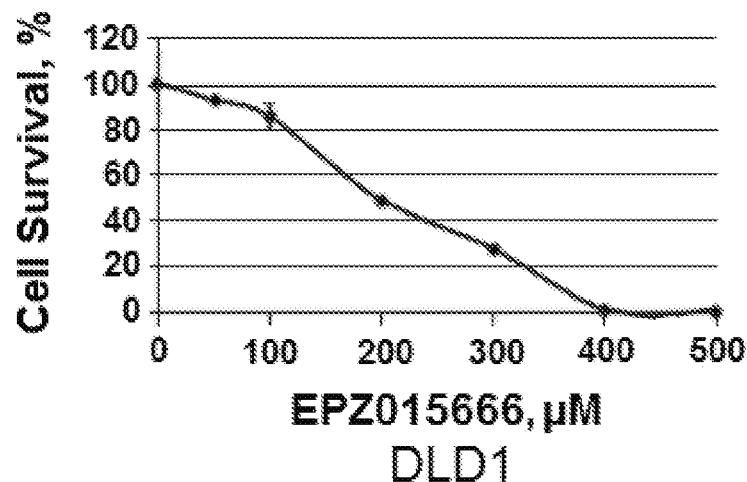

FIGS. 9A-G depict the results of experiments to determine the inhibitory effect of a commercially available PRMT5 inhibitor. FIGS. 9A-C are an MTT assay, showing that the commercially available PRMT5 inhibitor, EPZ015666, has lower efficacy to decrease cell viability in PDAC cells (PANC1, MiaPaCa2 and AsPC1) than that of compound (IIa). FIGS. 9D-F are an MTT assay, showing that EPZ015666 has lower efficacy to decrease cell viability in CRC cells (HT29, HCT116, and DLD1) than that of compound (IIa). The data represent the means±SD for three independent experiments. *P<0.05 vs. Ctrl group. FIG. 9G is a table summarizing the $IC_{50}$ values for EPZ015666 in PDAC and CRC cell lines, respectively.

Figure 10B:
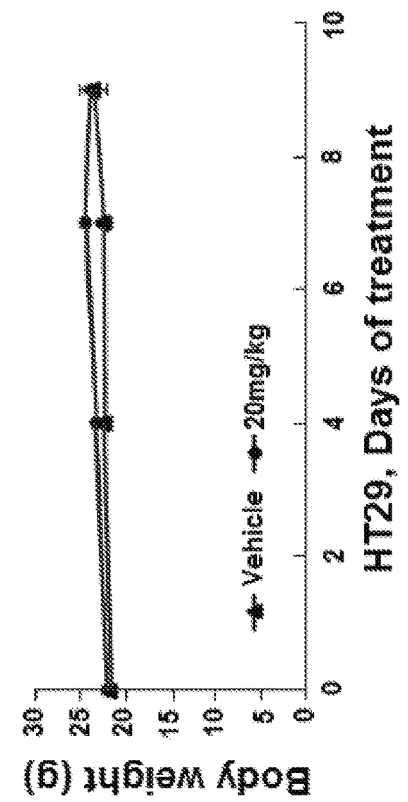
Figure 10A:
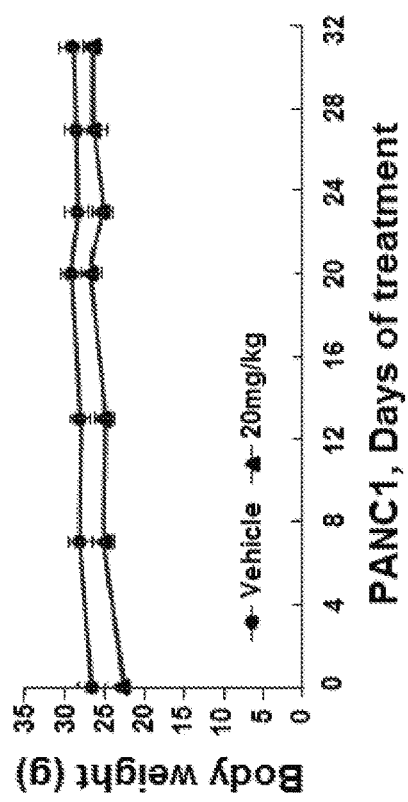
Figure 10D:
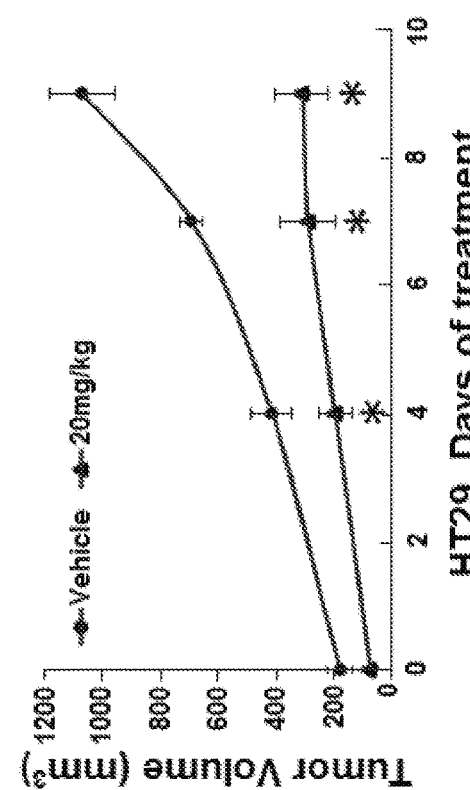
Figure 10C:
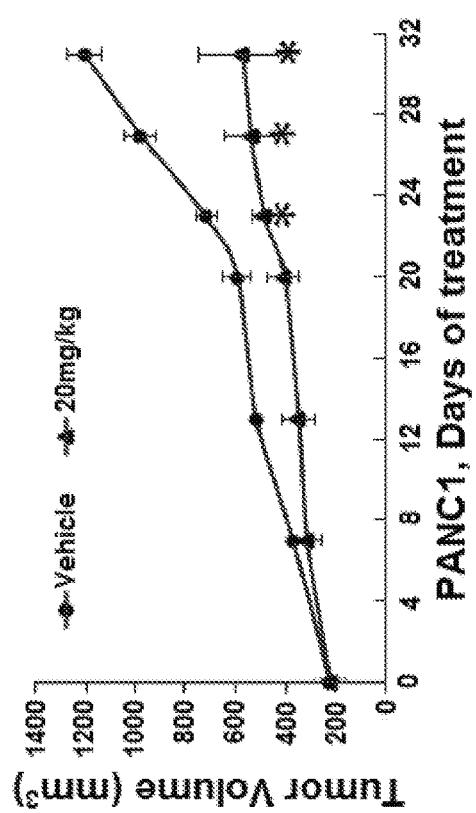

FIGS. 10A-D depict the results of experiments to determine the in vivo effect of compound (IIa). FIGS. 10A and 10B show that no significant changes in body weight were observed over the course of treatment in either PANC1 (FIG. 10A) or HT29 (FIG. 10B) model after treatment with 20 mg/kg of compound (IIa). (*P<0.05, n=4). FIGS. 10C and 10D are a tumor efficacy study, in which PANC1 (FIG. 10C) or HT29 (FIG. 10D) cells were subcutaneously implanted in NSG mice. Tumor volumes were measured and inhibition of tumor growth was observed upon treatment with 20 mg/kg of compound (IIa) intraperitoneally for 3x/week, as compared to the vehicle control. (*P<0.05, n=4).

Figure 11A:
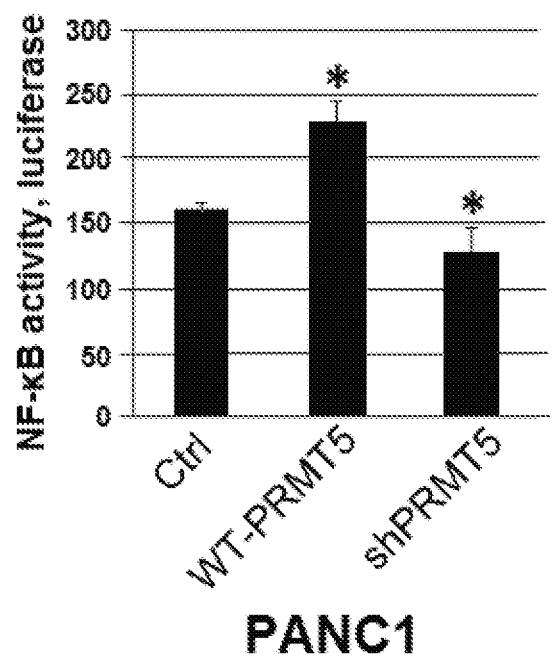
Figure 11B:
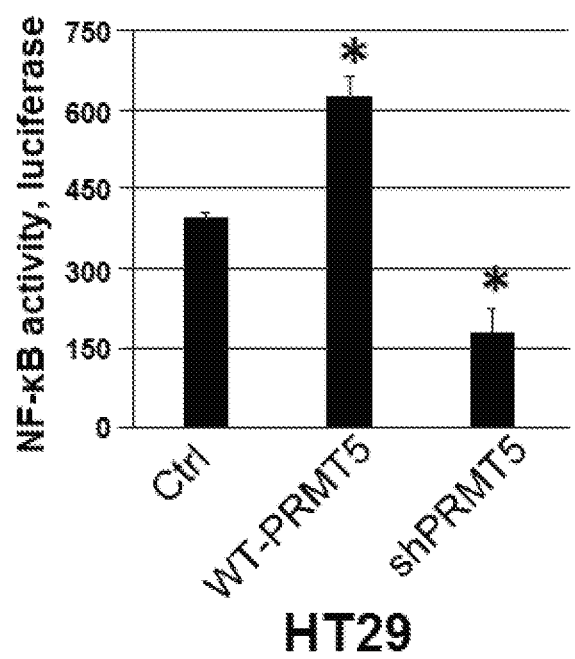
Figure 11C:
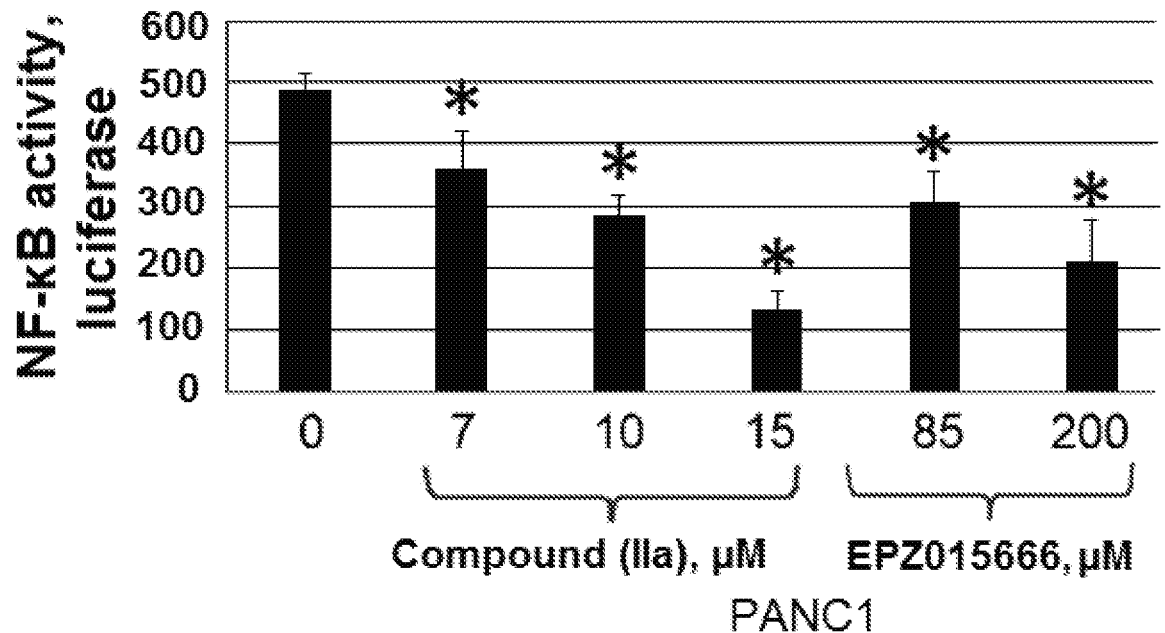
Figure 11D:
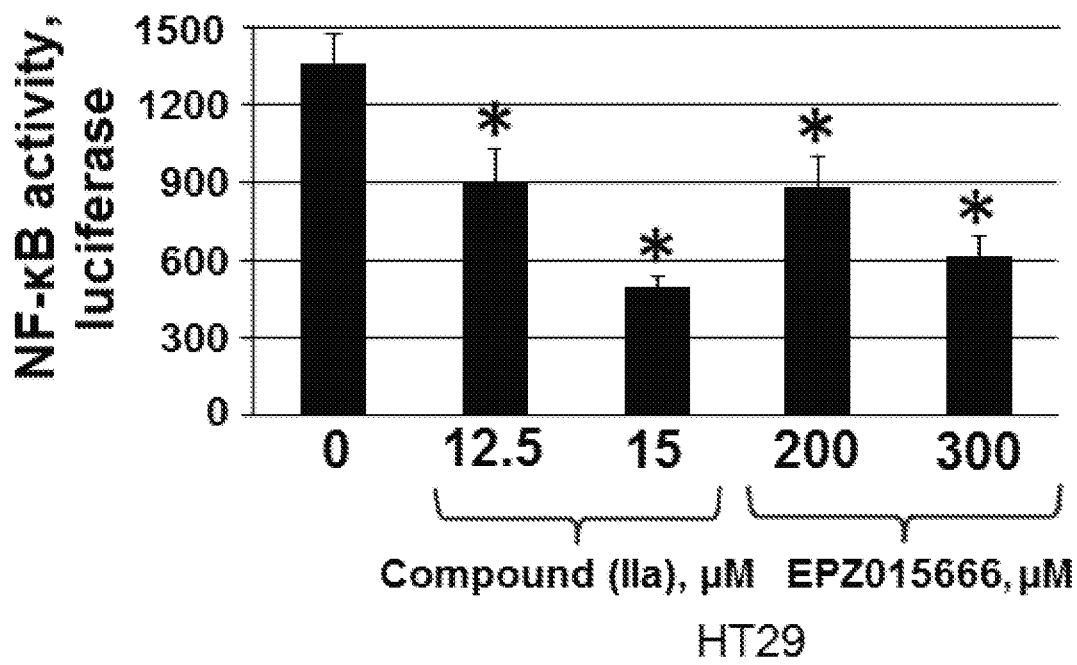
Figure 11E:
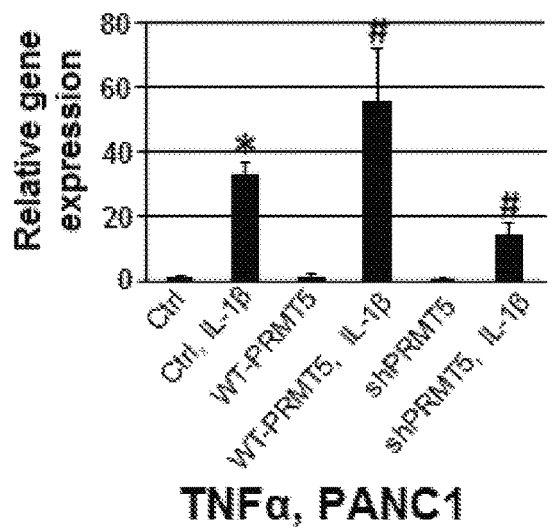
Figure 11F:
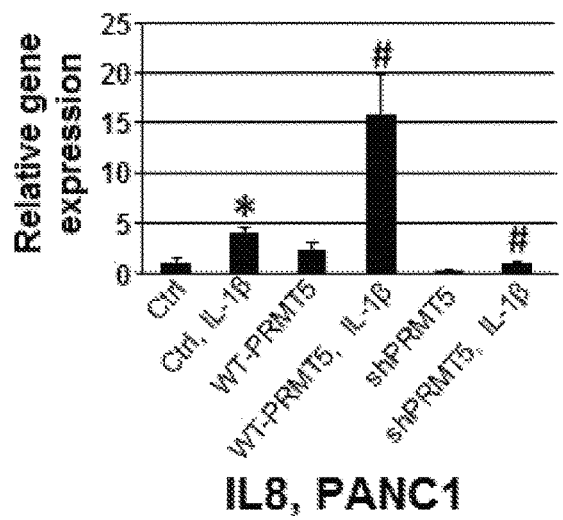
Figure 11G:
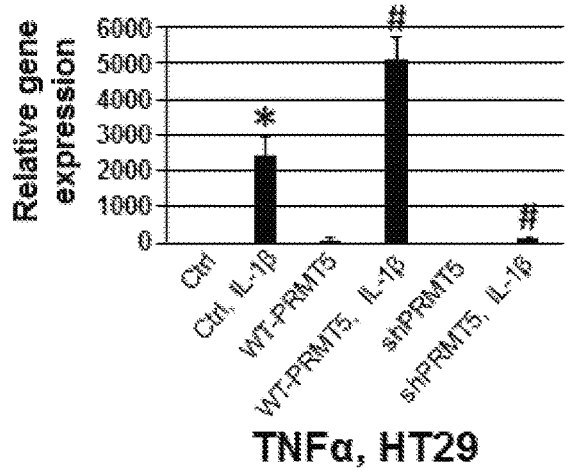
Figure 11H:
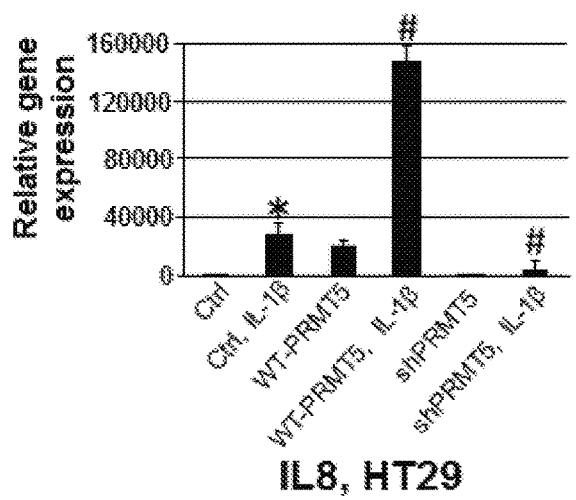
Figure 11I:
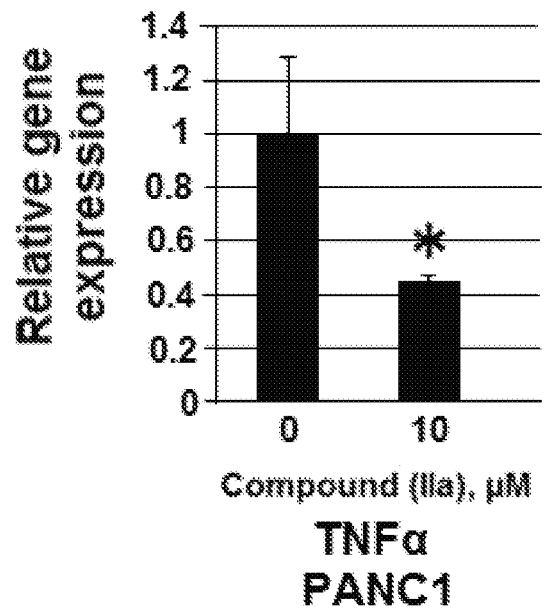
Figure 11J:
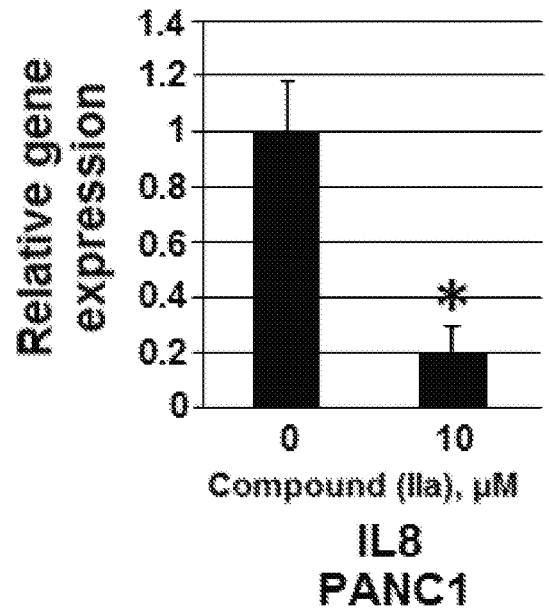
Figure 11K:
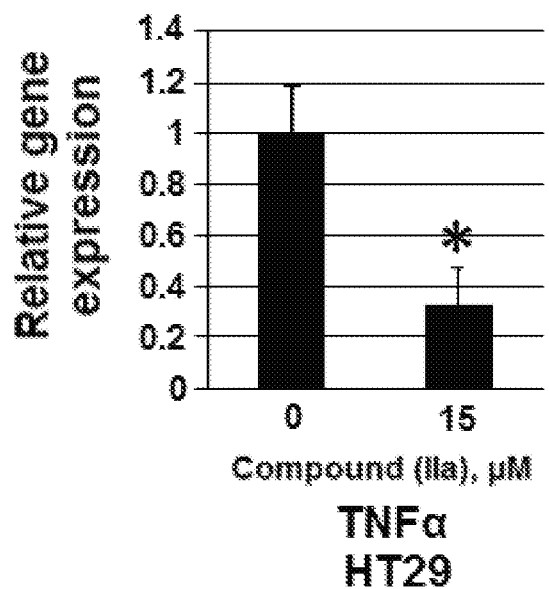
Figure 11L:
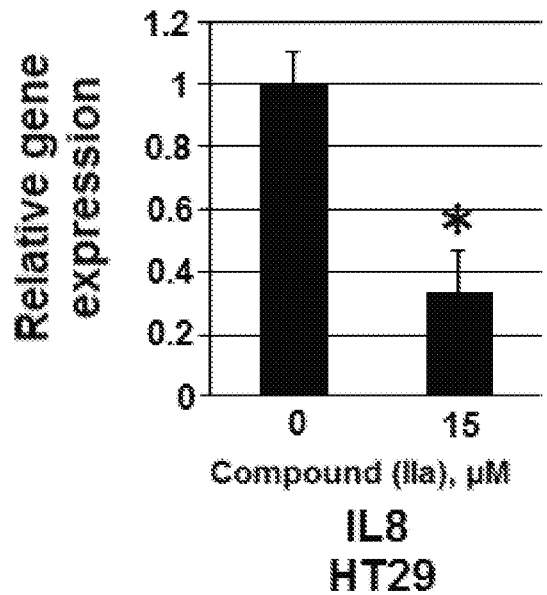

FIGS. 11A-L depicts the results of experiments to determine the effect of compound (IIa) on PRMT5 induced NF-κB activation. FIGS. 11A and 11B are a NF-κB luciferase assay, showing that overexpression of WT-PRMT5 led to NF-κB activation, while shPRMT5 resulted in the opposite effect in both PANC1 (FIG. 11A) and HT29 cells (FIG. 11B). FIGS. 11C and 11D are a luciferase assay, showing a decrease in NF-κB activation with increasing concentrations of compound (IIa) in PANC1 (FIG. 11C) and HT29 cells (FIG. 11D), respectively. EPZ015666 needed a higher concentration in order to reach a similar level of NF-κB inhibition as that of compound (IIa). The data represent the means±SD for three independent experiments. *P<0.05 vs. Ctrl group. FIGS. 11E-H is a qPCR analysis, showing that overexpression of PRMT5 significantly enhanced IL-1β-triggered typical NF-κB target genes expression, TNFα and IL8, while shPRMT5 exhibited the opposite effect, in both PANC1 (FIGS. 11E and 11F) and HT29 cells (FIGS. 11G and 11H). The data represent the means±SD for three independent experiments. *P<0.05 vs. Ctrl group; #P<0.05 vs. Ctrl+IL-1β-treated group. FIGS. 11I-L are a qPCR analysis, showing that treatment with compound (IIa) dramatically decreased NF-κB target genes (TNFα and IL8) expression, in both PANC1 (FIGS. 11I and 11J) and HT29 cells (FIGS. 11K and 11L). The data represent the means±SD for three independent experiments. *P<0.5 vs. Ctrl group.

FIGS. 12A-M depict the results of experiments to determine the inhibitory effect of compound (IIIa) and compound (IVa) in multiple cancer types. FIGS. 12A-12C are MTT assays in PDAC cells (PANC1 (FIG. 12A), MiaPaCa2 (FIG. 12B), and AsPC1 (FIG. 12C)), demonstrating that cell viability decreased significantly in the presence of increasing concentrations of compound (IIIa). FIGS. 12D-12F are MTT assays in CRC cells (HT29 (FIG. 12D), HTC116 (FIG. 12E), and DLD1 (FIG. 12F)), demonstrating that cell viability decreased significantly in the presence of increasing concentrations of compound (IIIa). FIGS. 12G-12I are MTT assays in PDAC cells (PANC1 (FIG. 12G), MiaPaCa2 (FIG. 12H), and AsPC1 (FIG. 12I)), demonstrating that cell viability decreased significantly in the presence of increasing concentrations of compound (IVa). FIGS. 12J-12L are MTT assays in CRC cells (HT29 (FIG. 12J), HTC116 (FIG. 12K), and DLD1 (FIG. 12L)), demonstrating that cell viability decreased significantly in the presence of increasing concentrations of compound (IVa). FIG. 12M is a table, summarizing the $IC_{50}$ values for compound (IIIa) and compound (IVa) in PDAC and CRC cells, respectively.

Figure 13A:
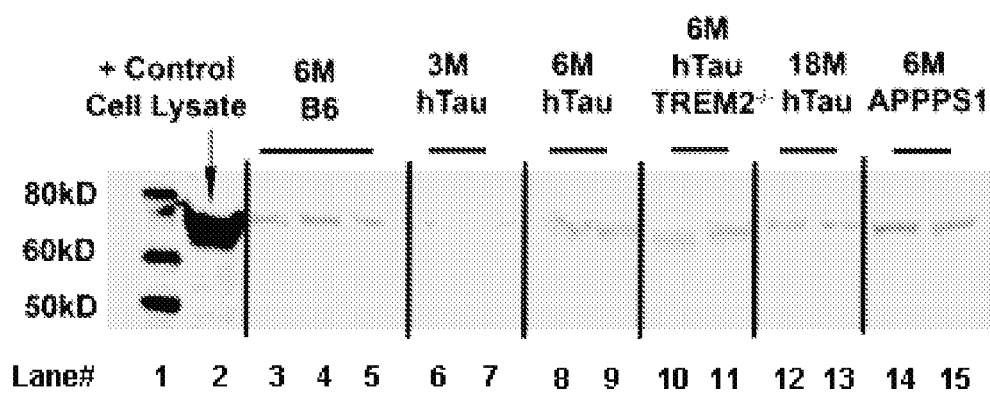
Figure 13B:
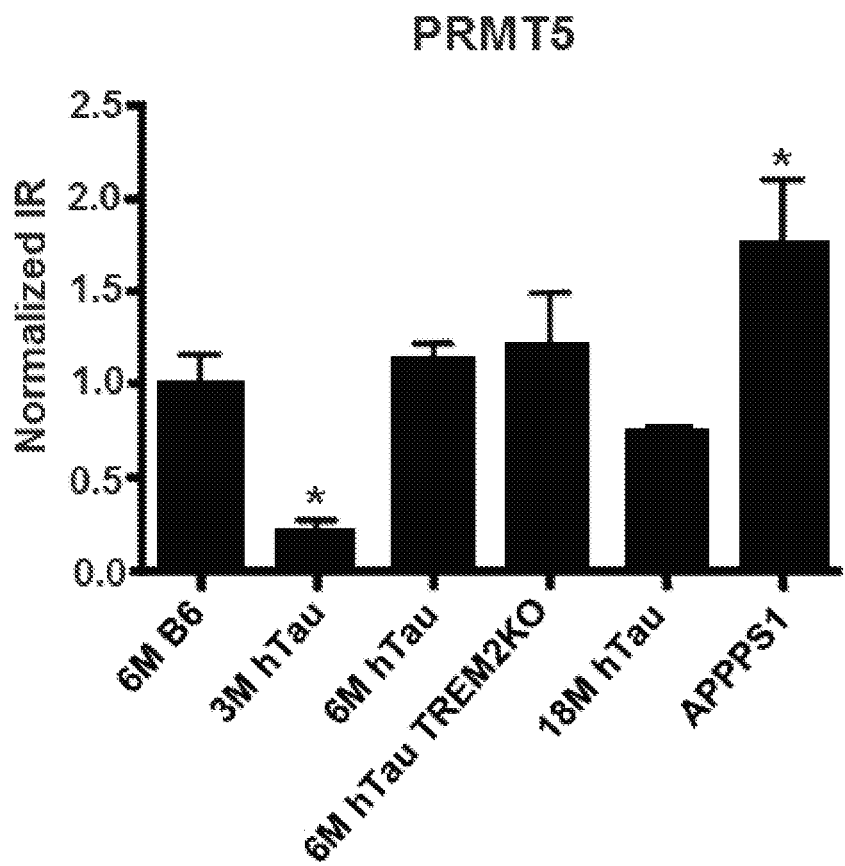

FIGS. 13A-B depict the results of experiments to identify the expression of PRMT5 in neurodegenerative disorders. FIG. 13A is a Western blot showing the expression of PRMT5 in cell lysate with PRMT5 overexpression (lane 2), non-transgenic B6 mice (6M) (lanes 3-5), hTau (humanized tau mice) (3M) (lanes 6-7), hTau (6M) (lanes 8-9), htau; Trem2−/− mice (6M) (lanes 10-11), hTau (18M) (lanes 12-13), and APPPS1 amyloid mice (lanes 14-15). FIG. 13B is a graph depicting the Western blot data of PRMT5 expression. *P<0.5 vs. Ctrl group.

Figure 14A:
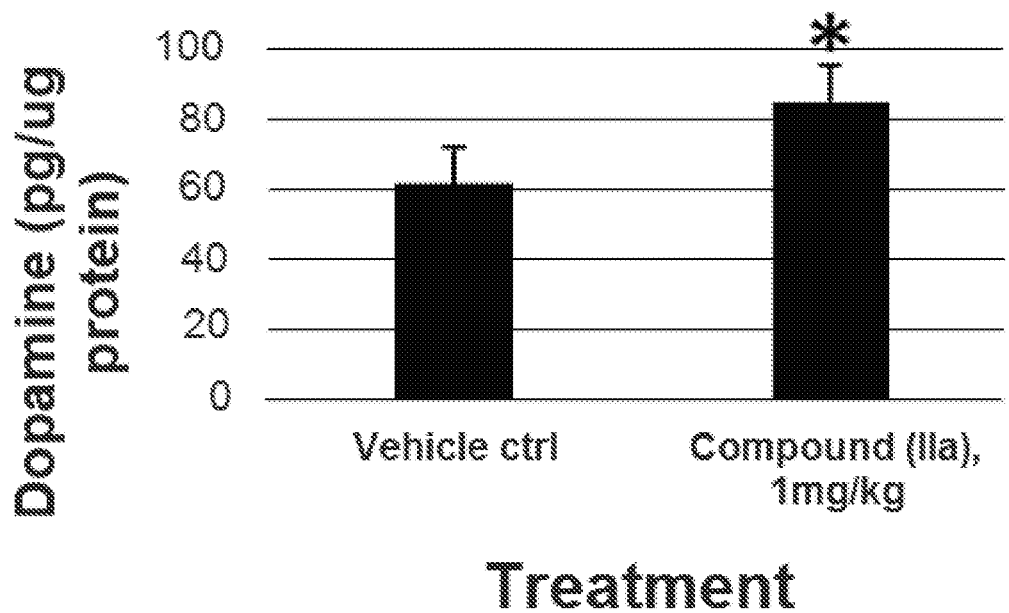
Figure 14B:
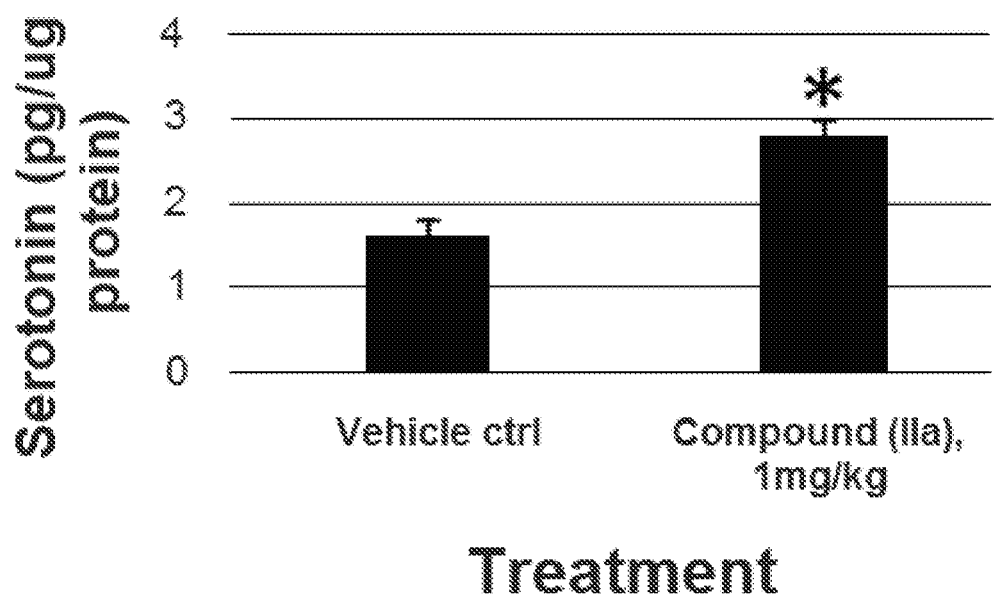

FIGS. 14A-B depicts the results of experiments to show the effect of compound (IIa) in neurological disorders. FIG. 14 shows the dopamine levels (FIG. 14A) and serotonin levels (FIG. 14B) in the striatum of rats treated with 7.5 mg/kg methamphetamine followed by 4 injections of 1 mg/kg compound (IIa) given at 12 hour intervals beginning 12 hours after methamphetamine treatment. (n=5). *P<0.05 vs. Ctrl group.

Figure 15:
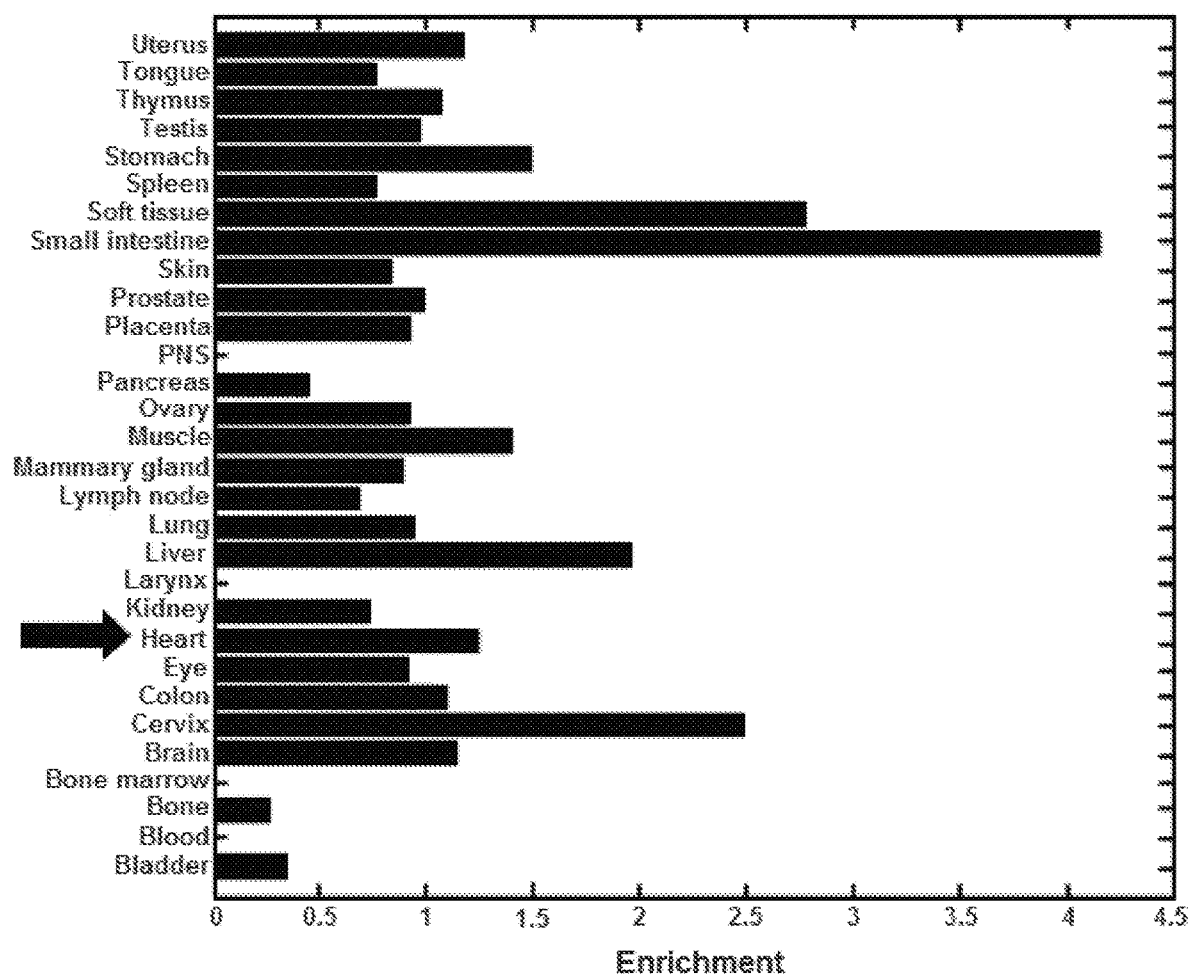

FIG. 15 is a graph showing the expression level of PRMT5 in multiple human tissues, including heart tissue, as determined using the TiGER database.

DETAILED DESCRIPTION OF THE INVENTION

The present invention is directed to compounds of formulas (I)-(IV) that have been discovered to be effective in inhibiting PRMT5, which enables the effective use of the compounds in treating various diseases associated with an increased expression or activity of PRMT5.

In particular, the present invention provides a compound of formula (I)

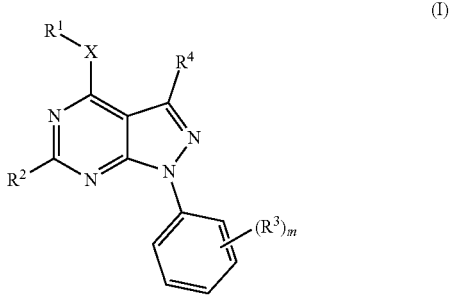

wherein
$R^1$ is hydrogen, halo, $C_1$-$C_8$ alkyl, $C_3$-$C_6$ cycloalkyl, heterocycloalkyl, aryl, or heteroaryl;
$R^2$ is $C_1$-$C_8$ alkyl, $C_2$-$C_8$ alkenyl, $C_3$-$C_6$ cycloalkyl, $C_3$-$C_6$ cycloalkylalkyl, heterocycloalkyl, aryl, arylalkyl, heteroaryl, $C_1$-$C_8$ alkoxy, $C_3$-$C_6$ cycloalkyloxy, aryloxy, halo, $C_1$-$C_8$ haloalkoxy, $C_1$-$C_8$ haloalkyl, haloaryl, haloaryloxy, —CN, —NO$_2$, —(CH$_2$)$_n$C(O)R$^5$, —(CH$_2$)$_n$CO$_2$R$^5$, —(CH$_2$)$_n$C(O)NR$^5$R$^6$, —(CH$_2$)$_n$NR$^5$C(O)R$^6$, or —(CH$_2$)$_n$NR$^5$R$^6$;

R$^3$ is hydroxy, $C_1$-$C_8$ alkyl, $C_2$-$C_8$ alkenyl, $C_3$-$C_6$ cycloalkyl, $C_3$-$C_6$ cycloalkylalkyl, $C_1$-$C_8$ alkoxy, $C_3$-$C_6$ cycloalkyloxy, heterocycloalkyl, aryl, arylalkyl, heteroaryl, aryloxy, halo, $C_1$-$C_8$ haloalkyl, $C_1$-$C_8$ haloalkoxy, haloaryl, haloaryloxy, —CN, —NO$_2$, —C(O)R$^5$, —CO$_2$R$^5$, —C(O)NR$^5$R$^6$, —NR$^5$C(O)R$^6$, —(CH$_2$)$_n$NR$^5$R$^6$, —(CH$_2$)$_n$SO$_2$NR$^5$R$^6$, —(CH$_2$)$_n$SO$_2$R$^5$, aryl; or two R$^3$ moieties and the phenyl group to which they are attached form a naphthyl group that is optionally substituted;

R$^4$ is H, hydroxy, $C_1$-$C_8$ alkyl, $C_2$-$C_8$ alkenyl, $C_3$-$C_6$ cycloalkyl, $C_1$-$C_8$ haloalkyl, —CN, —NO$_2$, —(CH$_2$)$_n$NR$^5$R$^6$, heterocycloalkyl, aryl, or heteroaryl;

X is a bond, —(CH$_2$)$_o$CR$^5$R$^6$—, —CR$^5$R$^6$(CH$_2$)$_o$—, —(CH$_2$)$_o$NR$^5$—, —NR$^5$(CH$_2$)$_o$—, —(CH$_2$)$_o$O—, or —O(CH$_2$)$_o$—, R$^5$ and R$^6$ are the same or different and each is H or $C_1$-$C_8$ alkyl;

m, n, and o are the same or different and each is 0 or an integer from 1-5, or a pharmaceutically acceptable salt thereof.

In an embodiment of the compound of formula (I), R$^1$ is hydrogen, halo, $C_1$-$C_8$ alkyl, $C_3$-$C_6$ cycloalkyl, aryl, heterocycloalkyl selected from the group consisting of isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl, or heteroaryl selected from the group consisting of pyridinyl, pyridazinyl, pyrimidyl, pyrazinyl, benzimidazolyl, triazinyl, imidazolyl, (1,2,3)-triazolyl, (1,2,4)-triazolyl, pyrazinyl, tetrazolyl, furyl, pyrrolyl, thienyl, isothiazolyl, thiazolyl, isoxazolyl, and oxadiazolyl. Preferably, R$^1$ is halo, heterocycloalkyl selected from the group consisting of isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl, or heteroaryl selected from the group consisting of pyridinyl, pyridazinyl, pyrimidyl, pyrazinyl, benzimidazolyl, triazinyl, imidazolyl, (1,2,3)-triazolyl, (1,2,4)-triazolyl, pyrazinyl, tetrazolyl, furyl, pyrrolyl, thienyl, isothiazolyl, thiazolyl, isoxazolyl, and oxadiazolyl.

In any of the foregoing embodiments of the compound of formula (I), R$^2$ is halo, $C_1$-$C_8$ haloalkoxy, $C_1$-$C_8$ haloalkyl, haloaryl, or haloaryloxy.

In any of the foregoing embodiments of the compound of formula (I), R$^3$ is $C_1$-$C_8$ alkyl, halo, or $C_1$-$C_8$ haloalkyl.

In any of the foregoing embodiments of the compound of formula (I), R$^4$ is H.

In any of the foregoing embodiments of the compound of formula (I), X is a bond, —(CH$_2$)$_o$NR$^5$—, or —NR$^5$(CH$_2$)$_o$—. Preferably, X is a bond or —NH(CH$_2$)$_o$— (e.g., —NH(CH$_2$)— or —NH(CH$_2$)$_2$—).

In any of the foregoing embodiments of the compound of formula (I), m is 1.

In any of the foregoing embodiments of the compound of formula (I), n is 0, 1, or 2.

In any of the foregoing embodiments of the compound of formula (I), o is 1 or 2.

In any of the foregoing embodiments of R$^5$ and R$^6$ are each H.

In any of the foregoing embodiments of the compound of formula (I), R$^1$ is heterocycloalkyl selected from the group consisting of isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl, or heteroaryl selected from the group consisting of pyridinyl, pyridazinyl, pyrimidyl, pyrazinyl, benzimidazolyl, triazinyl, imidazolyl, (1,2,3)-triazolyl, (1,2,4)-triazolyl, pyrazinyl, tetrazolyl, furyl, pyrrolyl, thienyl, isothiazolyl, thiazolyl, isoxazolyl, and oxadiazolyl.

In an embodiment of the compound of formula (I), R$^1$ is halo, heterocycloalkyl selected from the group consisting of isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl, or heteroaryl selected from the group consisting of pyridinyl, pyridazinyl, pyrimidyl, pyrazinyl, benzimidazolyl, triazinyl, imidazolyl, (1,2,3)-triazolyl, (1,2,4)-triazolyl, pyrazinyl, tetrazolyl, furyl, pyrrolyl, thienyl, isothiazolyl, thiazolyl, isoxazolyl, and oxadiazolyl; R$^2$ is halo; R$^3$ is $C_1$-$C_8$ alkyl or halo; R$^4$ is H; X is a bond or —NR$^5$(CH$_2$)$_o$—, R$^5$ is H; m is 1; and o is 1 or 2.

In an aspect of the invention, R$^1$ is heterocycloalkyl selected from the group consisting of isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl, or heteroaryl selected from the group consisting of pyridinyl, pyridazinyl, pyrimidyl, pyrazinyl, benzimidazolyl, triazinyl, imidazolyl, (1,2,3)-triazolyl, (1,2,4)-triazolyl, pyrazinyl, tetrazolyl, furyl, pyrrolyl, thienyl, isothiazolyl, thiazolyl, isoxazolyl, and oxadiazolyl; R$^2$ is halo; R$^3$ is $C_1$-$C_8$ alkyl or halo; R$^4$ is H; X is a bond or —NR$^5$(CH$_2$)$_o$—, R$^5$ is H; m is 1; and o is 1 or 2.

In any of the foregoing embodiments, the compound of formula (I) is in the form of a pharmaceutically acceptable salt.

Exemplary compounds of formula (I) include compounds (Ia), (Ib), (Ic), (Id), (Ie), (If), and (Ig), are set forth below. Pharmaceutically acceptable salts of these exemplary compounds are also envisioned.

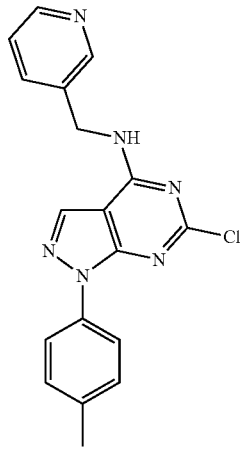
(Ia)

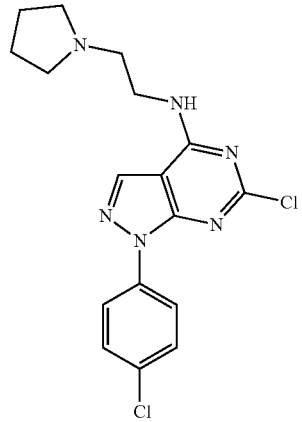
(Ib)

-continued (Ic)
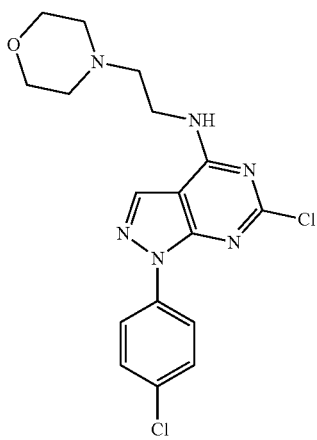

(Id)
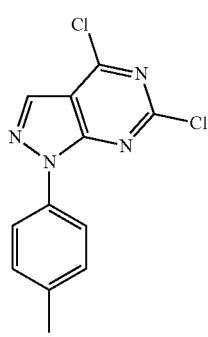

(Ie)
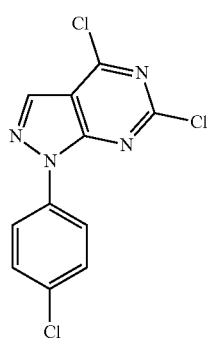

(If)
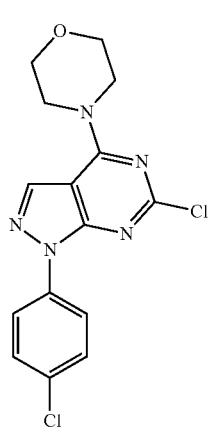

-continued (Ig)
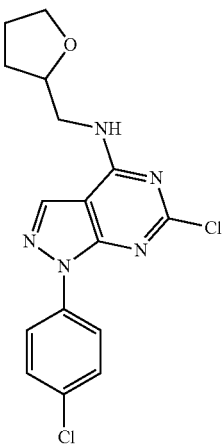

The present invention also provides a compound of formula (II):

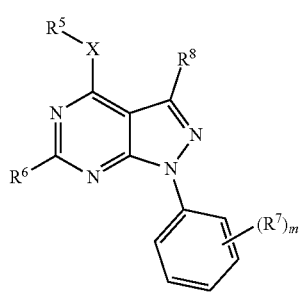

(II)

wherein
$R^5$ is halo, heterocycloalkyl, or heteroaryl;
$R^6$ is $C_1$-$C_8$ alkyl, $C_2$-$C_8$ alkenyl, $C_3$-$C_6$ cycloalkyl, $C_3$-$C_6$ cycloalkylalkyl, heterocycloalkyl, aryl, arylalkyl, heteroaryl, $C_1$-$C_8$ alkoxy, $C_3$-$C_6$ cycloalkyloxy, aryloxy, halo, $C_1$-$C_8$ haloalkoxy, $C_1$-$C_8$ haloalkyl, haloaryl, haloaryloxy, —CN, —NO$_2$, —(CH$_2$)$_n$C(O)R$^9$, —(CH$_2$)$_n$CO$_2$R$^9$, —(CH$_2$)$_n$C(O)NR$^9$R$^{10}$, —(CH$_2$)$_n$NR$^9$C(O)R$^{10}$, —(CH$_2$)$_n$NR$^9$R$^{10}$, —NR$^{11}$(CH$_2$)$_n$NR$^9$R$^{10}$; or
two $R^6$ moieties and the phenyl group to which they are attached form a naphthyl group that is optionally substituted;
$R^7$ is hydroxy, $C_1$-$C_8$ alkyl, $C_2$-$C_8$ alkenyl, $C_3$-$C_6$ cycloalkyl, $C_3$-$C_6$ cycloalkylalkyl, $C_1$-$C_8$ alkoxy, $C_3$-$C_6$ cycloalkyloxy, heterocycloalkyl, aryl, arylalkyl, heteroaryl, aryloxy, halo, $C_1$-$C_8$ haloalkyl, $C_1$-$C_8$ haloalkoxy, haloaryl, haloaryloxy, —CN, —NO$_2$, —C(O)R$^9$, —CO$_2$R$^9$, —C(O)NR$^9$R$^{10}$, —NR$^9$C(O)R$^{10}$, —(CH$_2$)$_n$NR$^9$R$^{10}$, —(CH$_2$)$_n$SO$_2$NR$^9$R$^{10}$, —(CH$_2$)$_n$SO$_2$R$^9$, aryl; or
two $R^7$ moieties and the phenyl group to which they are attached form a naphthyl group that is optionally substituted;
$R^8$ is H, hydroxy, $C_1$-$C_8$ alkyl, $C_2$-$C_8$ alkenyl, $C_3$-$C_6$ cycloalkyl, $C_1$-$C_8$ haloalkyl, —CN, —NO$_2$, —(CH$_2$)$_n$NR$^9$R$^{10}$, heterocycloalkyl, aryl, or heteroaryl;
X is a bond, —(CH$_2$)$_o$CR$^9$R$^{10}$—, —CR$^9$R$^{10}$(CH$_2$)$_o$—, —(CH$_2$)$_o$NR$^9$—, —NR$^9$(CH$_2$)$_o$—, —(CH$_2$)$_o$O—, or —O(CH$_2$)$_o$—,
$R^9$, $R^{10}$, and $R^{11}$ are the same or different and each is H or $C_1$-$C_8$ alkyl;
m, n, and o are the same or different and each is 0 or an integer from 1-5, or
a pharmaceutically acceptable salt thereof.

In an embodiment of the compound of formula (II), $R^1$ is hydrogen, halo, $C_1$-$C_8$ alkyl, $C_3$-$C_6$ cycloalkyl, aryl, heterocycloalkyl selected from the group consisting of isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl, or heteroaryl selected from the group consisting of pyridinyl, pyridazinyl, pyrimidyl, pyrazinyl, benzimidazolyl, triazinyl, imidazolyl, (1,2,3)-triazolyl, (1,2,4)-triazolyl, pyrazinyl, tetrazolyl, furyl, pyrrolyl, thienyl, isothiazolyl, thiazolyl, isoxazolyl, and oxadiazolyl. Preferably, $R^1$ is halo, heterocycloalkyl selected from the group consisting of isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl, or heteroaryl selected from the group consisting of pyridinyl, pyridazinyl, pyrimidyl, pyrazinyl, benzimidazolyl, triazinyl, imidazolyl, (1,2,3)-triazolyl, (1,2,4)-triazolyl, pyrazinyl, tetrazolyl, furyl, pyrrolyl, thienyl, isothiazolyl, thiazolyl, isoxazolyl, and oxadiazolyl. In another embodiment of the compound of formula (II), $R^1$ is substituted phenyl, as described herein, including phenyl substituted with $C_1$-$C_8$ alkyl, halo, or hydroxy. In a specific example, $R^1$ is 3,4-di-$C_1$-$C_8$ alkylphenyl (e.g., 3,4-dimethylphenyl).

In any of the foregoing embodiments of the compound of formula (II), $R^2$ is halo, $C_1$-$C_8$ haloalkoxy, $C_1$-$C_8$ haloalkyl, haloaryl, or haloaryloxy. Alternatively, $R^2$ is —$NR^7(CH_2)_n$ $NR^5R^6$. In an aspect of this embodiment, $R^5$ and $R^6$ are both $C_1$-$C_8$ alkyl, $R^7$ is H, and/or n is 1 or 2. Preferably, $R^2$ is —$NR^7(CH_2)_nNR^5R^6$; $R^5$ and $R^6$ are methyl; $R^7$ is H; and n is 2.

In any of the foregoing embodiments of the compound of formula (II), $R^3$ is $C_1$-$C_8$ alkyl, halo, or $C_1$-$C_8$ haloalkyl.

In any of the foregoing embodiments of the compound of formula (II), $R^4$ is H.

In any of the foregoing embodiments of the compound of formula (II), X is a bond, —$(CH_2)_oNR^5$—, or —$NR^5$ $(CH_2)_o$—. Preferably, X is a bond or —$NH(CH_2)_o$— (e.g., —NH—, —$NH(CH_2)$— or —$NH(CH_2)_2$—).

In any of the foregoing embodiments of the compound of formula (II), m is 0 or 1. In some preferred embodiments, m is 0, and the phenyl ring does not include any substituents.

In any of the foregoing embodiments of the compound of formula (I), n is 0, 1, or 2.

In any of the foregoing embodiments of the compound of formula (II), o is 0, 1, or 2.

In any of the foregoing embodiments of the compound of formula (II) $R^5$ and $R^6$ are each H.

An exemplary compound of formula (II) is compound (IIa). Pharmaceutically acceptable salts of the exemplary compound are also envisioned.

In any of the foregoing embodiments of the compound of formula (I) or formula (II), $R^1$ preferably is not chloro. In a preferred embodiment, the compound of formula (I) or (II) is not 4,6-dichloro-1-(p-tolyl)-1H-pyrazolo[3,4-d]pyrimidine or 4,6-dichloro-1-(4-chlorophenyl)-1H-pyrazolo[3,4-d]pyrimidine.

The present invention also provides a compound of formula (III):

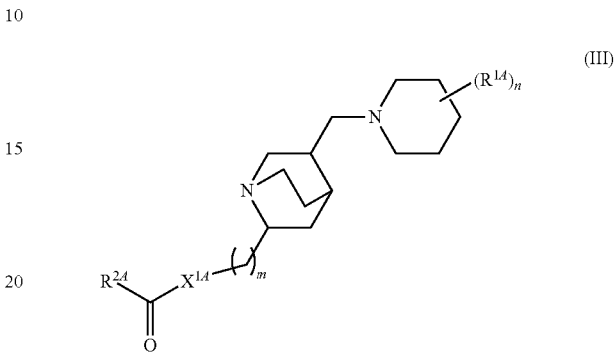

(III)

wherein $R^{1A}$ and $R^{2A}$ are the same or different and each is hydrogen, $C_1$-$C_8$ alkyl, $C_2$-$C_8$ alkenyl, $C_3$-$C_6$ cycloalkyl, $C_3$-$C_6$ cycloalkylalkyl, heterocycloalkyl, aryl, arylalkyl, heteroaryl, hydroxy, $C_1$-$C_8$ alkoxy, $C_3$-$C_6$ cycloalkyloxy, aryloxy, halo, $C_1$-$C_8$ haloalkoxy, $C_1$-$C_8$ haloalkyl, haloaryl, haloaryloxy, —CN, —$NO_2$, —$(CH_2)_nC(O)R^{11A}$—$(CH_2)_n$ $CO_2R^{11A}$, —$(CH_2)_nC(O)_nNR^{11A}R^{12A}$, —$(CH_2)_nNR^{11A}C(O)$ $R^{12A}$, or —$(CH_2)_nNR^{11A}R^{12A}$; wherein each moiety other than hydrogen, hydroxy, halo, —CN, and —$NO_2$ is optionally substituted;

$X^{1A}$ is O, S, or —$NR^{11A}$;

$R^{11A}$ and $R^{12A}$ are the same or different and each is H or $C_1$-$C_8$ alkyl;

m is an integer from 1-4; and n is 0 or an integer from 1-5, or a pharmaceutically acceptable salt thereof.

An exemplary compound of formula (III) is compound (IIIa). Pharmaceutically acceptable salts of the exemplary compound also are envisioned.

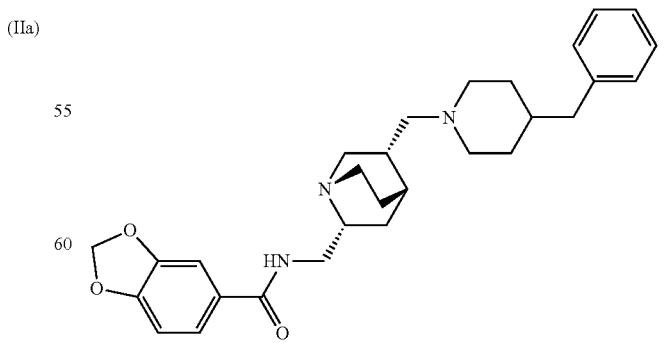

(IIIa)

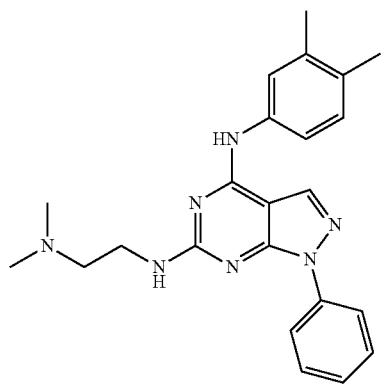

(IIa)

The present invention further provides a compound of formula (IV):

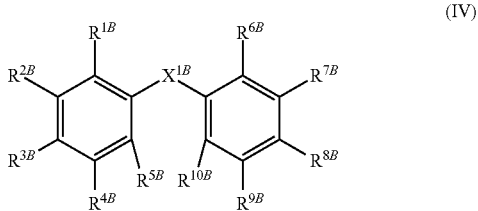

(IV)

wherein $R^{1B}$, $R^{2B}$, $R^{3B}$, $R^{4B}$, $R^{5B}$, $R^{6B}$, $R^{7B}$, $R^{8B}$, $R^{9B}$, and $R^{10B}$ are the same or different and each is hydrogen, $C_1$-$C_8$ alkyl, $C_2$-$C_8$ alkenyl, $C_3$-$C_6$ cycloalkyl, $C_3$-$C_6$ cycloalkylalkyl, heterocycloalkyl, aryl, arylalkyl, heteroaryl, hydroxy, $C_1$-$C_8$ alkoxy, $C_3$-$C_6$ cycloalkyloxy, aryloxy, halo, $C_1$-$C_8$ haloalkoxy, $C_1$-$C_8$ haloalkyl, haloaryl, haloaryloxy, —CN, —NO$_2$, —(CH$_2$)$_n$C(O)R$^{11A}$, —(CH$_2$)$_n$CO$_2$R$^{11A}$, —(CH$_2$)$_n$C(O)NR$^{11A}$R$^{12A}$, —(CH$_2$)$_n$NR$^{11A}$C(O)R$^{12A}$, or —(CH$_2$)$_n$NR$^{11A}$R$^{12A}$; wherein each moiety other than hydrogen, hydroxy, halo, —CN, and —NO$_2$ is optionally substituted;

$X^{1B}$ is O, S, or —NR$^{11B}$; and $R^{11B}$ and $R^{12B}$ are the same or different and each is H or $C_1$-$C_8$ alkyl, or a pharmaceutically acceptable salt thereof.

An exemplary compound of formula (IV) is compound (IVa). Pharmaceutically acceptable salts of the exemplary compound are also envisioned.

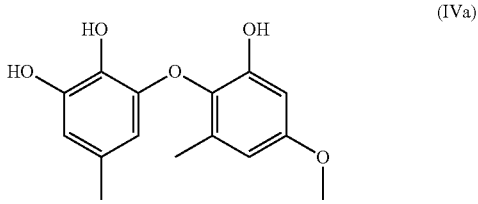 [SMILES: COc1cc(C)c(Oc2cc(C)cc(O)c2O)c(O)c1]

(IVa)

In any of the embodiments above, the term "alkyl" implies a straight-chain or branched alkyl substituent containing from, for example, from about 1 to about 8 carbon atoms, e.g., from about 1 to about 6 carbon atoms. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs as part of a group, such as, e.g., in $C_3$-$C_6$ cycloalkylalkyl, hydroxyalkyl, haloalkyl (e.g., monohaloalkyl, dihaloalkyl, and trihaloalkyl), cyanoalkyl, aminoalkyl, alkylamino, dialkylamino, arylalkyl, etc. The alkyl can be substituted or unsubstituted, as described herein. Even in instances in which the alkyl is an alkylene chain (e.g., —(CH$_2$)$_n$—), the alkyl group can be substituted or unsubstituted. An example of a substituted alkylene chain includes —CF$_2$-cyclopropyl.

In any of the embodiments above, the term "alkenyl," as used herein, means a linear alkenyl substituent containing from, for example, about 2 to about 8 carbon atoms (branched alkenyls are about 3 to about 8 carbons atoms), e.g., from about 3 to about 6 carbon atoms (branched alkenyls are about 3 to about 6 carbons atoms). In accordance with an embodiment, the alkenyl group is a $C_2$-$C_4$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like. The alkenyl can be substituted or unsubstituted, as described herein.

In any of the embodiments above, the term "cycloalkyl," as used herein, means a cyclic alkyl moiety containing from, for example, 3 to 6 carbon atoms or from 5 to 6 carbon atoms. Examples of such moieties include cyclopropyl, cyclobutyl, cyclopentyl, cyclohexyl, and the like. The cycloalkyl can be substituted or unsubstituted, as described herein. For example, a substituted cycloalkyl includes a halo- or haloalkyl-substituted cyclopropyl, such as 2-fluorocyclopropyl, 2,2-difluorocyclopropyl, 1-(trifluoromethyl)cyclopropyl, and 2-(trifluoromethyl)cyclopropyl.

In any of the embodiments above, the term "hydroxy" refers to the group —OH.

In any of the embodiments above, the terms "alkoxy" and "cycloalkyloxy" embrace linear or branched alkyl and cycloalkyl groups, respectively, that are attached to a divalent oxygen. The alkyl and cycloalkyl groups are the same as described herein. The term "aryloxy" refers to substituents that have an aryl group attached to divalent oxygen. The aryl group is the same as described herein.

In any of the embodiments above, the term "halo" refers to a halogen selected from fluorine, chlorine, bromine, and iodine.

In any of the embodiments above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise 4n+2 π electrons, according to Hückel's Rule, wherein n=1, 2, or 3. This definition also applies wherever "aryl" occurs as part of a group, such as, e.g., in haloaryl (e.g., monohaloaryl, dihaloaryl, and trihaloaryl), arylalkyl, etc. The aryl can be substituted or unsubstituted, as described herein.

In any of the embodiments above, the term "heteroaryl" refers to aromatic 5 or 6 membered monocyclic groups, 9 or 10 membered bicyclic groups, and 11 to 14 membered tricyclic groups which have at least one heteroatom (O, S, or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, pyrrolyl, thienyl, isothiazolyl, thiazolyl, isoxazolyl, and oxadiazolyl. The heteroaryl can be substituted or unsubstituted, as described herein.

The term "heterocycloalkyl" means a stable, saturated, or partially unsaturated monocyclic, bicyclic, and spiro ring system containing 3 to 7 ring members of carbon atoms and other atoms selected from nitrogen, sulfur, and/or oxygen. In an aspect, a heterocycloalkyl is a 5, 6, or 7-membered monocyclic ring and contains one, two, or three heteroatoms selected from nitrogen, oxygen, and sulfur. The heterocycloalkyl may be attached to the parent structure through a carbon atom or through any heteroatom of the heterocycloalkyl that results in a stable structure. Examples of such heterocycloalkyl rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl. The heterocycloalkyl can be substituted or unsubstituted, as described herein.

In any of the embodiments above, the alkyl, alkoxy, and alkylamino groups can be linear or branched.

In other aspects, any substituent that is not hydrogen (e.g., $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, aryl, arylalkyl, heteroaryl, heteroarylalkyl, or heterocycloalkyl) can be an optionally substituted moiety. The substituted moiety typically comprises at least one substituent (e.g., 1, 2, 3, 4, 5, 6, etc.) in any suitable position (e.g., 1-, 2-, 3-, 4-, 5-, or 6-position, etc.). When an aryl group is substituted with a substituent, e.g., halo, amino, alkyl, OH, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention. Suitable substituents include, e.g., halo, alkyl, alkenyl, alkynyl, hydroxy, nitro, cyano, amino, alkylamino, alkoxy, aryloxy, aralkoxy, carboxyl, carboxyalkyl, carboxyalkyloxy, amido, alkylamido, haloalkylamido, aryl, heteroaryl, and heterocycloalkyl, each of which is described herein. In some instances, the substituent is at least one alkyl, halo, and/or haloalkyl (e.g., 1 or 2).

In any of the embodiments above, whenever a range of the number of atoms in a structure is indicated (e.g., a $C_{1-12}$, $C_{1-8}$, $C_{1-6}$, or $C_{1-4}$ alkyl, cycloalkyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, cycloalkyl, etc.) referenced herein encompasses and specifically describes 1, 2, 3, 4, 5, 6, 7, and/or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, etc., as appropriate).

The subscript "m" represent the number of substituents of $R^3$, in which each substituent of $R^3$, can be the same or different. The subscripts m can be either 0 or an integer from 1-5 (i.e., 1, 2, 3, 4, or 5). When m is 0, then the $R^3$ is not present in the compound of formula (I) or (II). The subscripts "n" and "o" represent the number of methylene repeat units. The subscripts n and o are either 0 or an integer from 1-5 (i.e., 1, 2, 3, 4, or 5). When n or o is 0, then the respective moiety does not contain any methylene repeat units.

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, nonaqueous media such as ether, ethyl acetate, ethanol, isopropanol, or acetonitrile are typical. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium.

The methods described herein comprise administering a compound of formula (I), formula (II), formula (III), or formula (IV), or a pharmaceutically acceptable salt thereof in the form of a pharmaceutical composition. In particular, a pharmaceutical composition will comprise at least one compound of formulas (I)-(IV), or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of formula (I), formula (II), formula (III), or formula (IV), or a pharmaceutically acceptable salt thereof can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I), formula (II), formula (III), or formula (IV), or a pharmaceutically acceptable salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the inhibitors in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The inhibitors may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of formula (I), formula (II), formula (III), or formula (IV), or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

The dose administered to the subject, particularly human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

The inventive methods comprise administering a pharmaceutically effective amount of a compound of formula (I), formula (II), formula (III), or formula (IV), or a pharmaceutically acceptable salt thereof for the treatment of a disease. As used herein, the terms "treatment," "treated," "treating," and the like refer to obtaining a desired pharmacologic and/or physiological effect. Preferably, the effect is therapeutic, i.e., the effect partially or completely cures a disease and/or adverse symptom attributable to the disease. A "pharmaceutically effective amount" means an amount sufficient to show a meaningful benefit in an individual, e.g., promoting at least one aspect of tumor cell cytotoxicity (e.g., inhibition of growth, inhibiting survival of a cancer cell, reducing proliferation, reducing size and/or mass of a tumor (e.g., solid tumor)), or treatment, healing, prevention, delay of onset, halting, or amelioration of other relevant medical condition(s) associated with a particular cancer. The meaningful benefit observed in the patient can be to any suitable degree (e.g., at least 10%, at least 20%, at least 30%, at least 40%, at least 50%, at least 60%, at least 70%, at least 80%, or 90% or more). In some aspects, one or more symptoms of the cancer are prevented, reduced, halted, or eliminated subsequent to administration of a compound of formula (I), formula (II), formula (III), or formula (IV), including compounds of formula (Ia), (Ib), (Ic), (Id), (Ie), (If), (Ig), (IIa), (IIIa), and (IVa), or a pharmaceutically acceptable salt thereof, thereby effectively treating the cancer to at least some degree.

Effective amounts can vary depending upon the biological effect desired in the individual, condition to be treated, and/or the specific characteristics of the compound of formula (I), formula (II), formula (III), or formula (IV), including compounds of formula (Ia), (Ib), (Ic), (Id), (Ie), (If), (Ig), (IIa), (IIIa), and (IVa), or a pharmaceutically acceptable salt thereof, and the individual. In this respect, any suitable dose of the compound of formula (I), formula (II), formula (III), or formula (IV), or a pharmaceutically acceptable salt thereof can be administered to the patient (e.g., human), according to the type of disease (e.g., cancer) to be treated. Various general considerations taken into account in determining the "effective amount" are known to those of skill in the art and are described, e.g., in Gilman et al., Eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I), formula (II), formula (III), or formula (IV), including compounds of formula (Ia), (Ib), (Ic), (Id), (Ie), (If), (Ig), (IIa), (IIIa), and (IVa), or a pharmaceutically acceptable salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound formula (I), formula (II), formula (III), or formula (IV), or a pharmaceutically acceptable salt thereof, comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

In an aspect of the invention, a compound of formula (I), a compound of formula (II), a compound of formula (III), or a compound of formula (IV), or a pharmaceutically acceptable salt thereof can inhibit the activity of PRMT5 in a cell. Elevated activity of PRMT5 has been described in the art for multiple disorders, including various types of cancer (Wei et al., *Proc. Natl. Acad. Sci.,* 110(33): 13516-13521 (2013); Lu et al., *Cancer Res.,* 75(18): 3692-3695 (2015)). While not wishing to be bound by any particular theory, it is believed that inhibition of PRMT5 by a compound of formula (I), a compound of formula (II), a compound of formula (III), or a compound of formula (IV), or a pharmaceutically acceptable salt thereof causes a decrease in the activation of nuclear factor κB (NF-κB) leading to a decrease in tumor progression.

As used herein the terms "elevated activity," "increased activity" and the like refers to any increase in the enzymatic activity of the protein, any increase in the total amount of protein present, or any increase in the level of gene (e.g., mRNA, RNA, DNA) expression. Increased activity is measured against a control sample. For example, the mRNA level of PRMT5 is measured in a cancer cell and is compared to the PRMT5 mRNA level in a non-cancer control cell of the same tissue type. Methods to identify subjects or cells with increased activity of a protein, increased level of a protein, or increased expression of a gene are routine in the art and include, for example, Western blotting, RT-PCR, PCR, quantitative PCR, ELISA, and enzyme assays. Additionally, the methods described herein can also be used by a person of ordinary skill in the art to determine increased activity of a protein, increased level of a protein or increased expression of a gene.

One aspect of the inventive method provides a method of treating cancer in a subject comprising administering a pharmaceutically effective amount of formula (I), formula (II), formula (III), or formula (IV), which includes the compounds of formulas (Ia), (Ib), (Ic), (Id), (Ie), (If), (Ig), (IIa), (IIIa), and (IVa), or a pharmaceutically acceptable salt thereof, to the subject whereby the cancer is treated.

As used herein the term "subject" includes any living organism that would benefit from inhibition of PRMT5. In certain embodiments the subject is a mammal. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the invention, the subject is a human.

The type of cancer is not particularly limited. In certain embodiments the cancer is characterized as a cancer that has increased activity of PRMT5 compared to a non-cancer sample of the same tissue type. The identification of a cancer that has increased activity of PRMT5 can be readily identified by a person of ordinary skill in the art using routine methods (e.g., Western blot, enzyme-linked immunosorbent assay (ELISA), or polymerase chain reaction (PCR)), including the methods described herein. In another embodiment the cancer is characterized as a cancer that has increased activity of NF-κB compared to a non-cancer sample of the same tissue type. The identification of a cancer that has increased activity of NF-κB can be readily identified by a person of ordinary skill in the art using routine methods (e.g., Western blot, ELISA, or PCR). In a further embodiment of the invention the cancer has increased activity of PRMT5 and increased activity of NF-κB.

Examples of cancers treatable with the inventive method include cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., Eds., pp. 491 762 (15th ed. 2001). In some aspects, the cancer is a solid tumor. In accordance with an embodiment, the cancer is selected from gastrointestinal cancer, skin cancer, lung cancer, brain cancer, ovarian cancer, prostate cancer, lymphoma, melanoma, and breast cancer. In another embodiment, the cancer is pancreatic ductal adenocarcinoma (PDAC), colorectal cancer, pancreatic cancer, or liver cancer.

Another aspect of the inventive method provides a method of inhibiting the activity of PRMT5 in a cell, comprising administering a pharmaceutically effective amount of a compound of formula (I), formula (II), formula (III), or formula (IV), or a pharmaceutically acceptable salt thereof to the cell, whereby the activity of PRMT5 is inhibited. Inhibition of PRMT5 includes any decrease in methyltransferase activity compared to an untreated or control treated subject. Inhibition or PRMT5 also includes any decrease in the protein level of PRMT5 in a subject compared to an untreated or control treated subject. Inhibition of PRMT5 can be demonstrated, for example, by a decrease in NF-κB activity.

In certain embodiments the cell is treated in vitro or ex vivo. In other embodiments the cell is in a subject.

The type of cell in which PRMT5 is inhibited is not particularly limited. In certain embodiments, the cell is a cancer cell. The cancer cell can be from any cancer type described in the foregoing. In certain embodiments the cancer cell is from PDAC, colorectal cancer, pancreatic cancer, or liver cancer.

PRMT5 activity has been shown to be increased in a variety of disease, and inhibition of PRMT5 has been described in the art as a viable treatment of multiple diseases, including autoimmune diseases, inflammatory disease, metabolic disorders, neurological and neurodegenerative disorders, cardiovascular diseases, and blood disorders (Kim et al., *Mediators Inflamm.*, 2016; Published online doi: 10.1155/2016/4028353; Stopa et al., *Cell Mol. Life Sci.*, 2015; 72(11): 2041-2059; Karkhanis et al., *Trends Biochem Sci.*, 2011; 36(12): 633-641; Likhite et al., *Science Signaling*, 2015; 8(402) ra115; Wei et al., *Cell Cycle*, 2013; 13: 32-41; Kryukov et al. *Science*, 2016; epub 10.1126/science.aad5214). Therefore, another aspect of the invention provides a method of treating a disease associated with increased expression of PRMT5 in a subject, comprising administering a pharmaceutically effective amount of a compound of formula (I), formula (II), formula (III), or formula (IV), or a pharmaceutically acceptable salt thereof to the subject, thereby treating the disease. Suitable diseases that can be treated include, for example, autoimmune diseases, inflammatory disease, metabolic disorders, neurological and neurodegenerative disorders, cardiovascular diseases, and blood disorders.

Examples of autoimmune diseases treatable with the inventive method include alopecia areata, autoimmune hemolytic anemia, autoimmune hepatitis, dermatomyositis, diabetes (type 1), juvenile idiopathic arthritis, glomerulonephritis, Graves' disease, Guillain-Barré syndrome, idiopathic thrombocytopenic purpura, myasthenia gravis, myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, thyroiditis, uveitis, vitiligo, and granulomatosis with polyangiitis (Wegener's).

Examples of inflammatory diseases treatable with the inventive method include ankylosing spondylitis, arthritis (e.g., osteoarthritis, rheumatoid arthritis (RA), psoriatic arthritis), gout, eczema, gastritis, splenitis, sinusitis, hepatitis, nephritis, psoriasis, vasculitis, atherosclerosis, sarcoidosis, pleurisy, asthma, atherosclerosis, Crohn's disease, colitis, dermatitis, diverticulitis, fibromyalgia, hepatitis, irritable bowel syndrome (IBS), systemic lupus erythematous (SLE), nephritis, and ulcerative colitis.

Examples of metabolic disorders treatable with the inventive method include diabetes (type 1 and type 2), phenylketonuira, and obesity.

Examples of neurological and neurodegenerative disorders treatable with the inventive method include drug abuse (e.g., methamphetamine addiction), Alzheimer's disease, amyotrophic lateral sclerosis, Angelman syndrome, Asperger syndrome, autism, bipolar disorder, cerebral arteriosclerosis, Charcot-Marie-Tooth disease, chronic pain, Cushing's syndrome, Creutzfeldt-Jakob disease, dementia, Huntington's disease, inclusion body myositis, Parkinson's disease, and Reye syndrome.

Examples of cardiovascular disorders treatable with the inventive method include coronary artery disease, angina, myocardial infarction, stroke, hypertensive heart disease, rheumatic heart disease, cardiomyopathy, arrhythmia, congenital heart disease, valvular heart disease, carditis, aortic aneurysms, peripheral artery disease, and venous thrombosis.

Examples of blood disorders treatable with the inventive method include anemia, bleeding disorders, hemophilia, sickle cell anemia, hemoglobinopathy, β-thalassemia, and blood clots.

In certain embodiments of this method, a compound formula (I), a compound of formula (II), a compound of formula (III), or a compound of formula (IV), or a pharmaceutically acceptable salt thereof can be co-administered with an anti-cancer agent (e.g., a chemotherapeutic agent) and/or radiation therapy. In an aspect, the method comprises administering an amount of a compound or salt that is effective to sensitize the cancer cells to one or more therapeutic regimens (e.g., chemotherapy or radiation therapy). The terms "co-administered" or "co-administration" refer to simultaneous or sequential administration. A compound may be administered before, concurrently with, or after administration of another compound.

One or more than one, e.g., two, three, or more anti-cancer agents can be administered. In this regard, the present invention is directed a pharmaceutical composition comprising a pharmaceutically acceptable carrier and a combination of a compound of formula (I), a compound of formula (II), a compound of formula (III), or a compound of formula (IV), or a pharmaceutically acceptable salt thereof and at least one anti-cancer agent (e.g., chemotherapeutic agent).

Examples of anti-cancer agents include platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mytomycin C, plicamycin, dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteasome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicaluatmide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, or any combination thereof.

In other embodiments of this method, a compound formula (I), a compound of formula (II), a compound of formula (III), or a compound of formula (IV), or a pharmaceutically acceptable salt thereof can be co-administered with an agent that treats a disease associated with increased activity of PRMT5.

One or more than one, e.g., two, three, or more agents can be administered. In this regard, the present invention is directed a pharmaceutical composition comprising a pharmaceutically acceptable carrier and a combination of a compound of formula (I), a compound of formula (II), a compound of formula (III), or a compound of formula (IV), or a pharmaceutically acceptable salt thereof and at least one other PRMT5 disease modifying agent.

Examples of autoimmune disease and inflammatory disease treating agents include alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antimetabolites (e.g., methotrexate, azathioprine, mercaptopurine, flurouracil), cytotoxic antibiotics (e.g., daunorubicin, doxorubicin, idarubicin, epirubicin, mitoxantrone, bleomycin, mytomycin C, plicamycin, dactinomycin), polyclonal antibodies (e.g., atgam, thymoglobuline), monoclonal antibodies (e.g., muromonab-CD3, basiliximab, daclizumab, omalizumab), calcinurin and mTOR inhibitors (e.g., ciclosporin, tacrolumus, sirolimus, everolimus),), biological agents (e.g., interferons and interleukins), opioids, TNF binding proteins (e.g., infliximab, etanercept, adalimumab, curcumin catechins), nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, disease-modifying antirheumatic drugs (DMARDS) (e.g., hydroxychloroquine, leflunomide, minocycline, anakinra, abatacept, azathioprine, tofacitinib), steroids (e.g., glucocorticoids, cortisol, prednisone, dexamethasone, and prednisolone), or any combination thereof.

Examples of metabolic disorder treating agents include short-acting insulin (e.g., humulin, novolin), rapid-acting insulin (e.g., insulin aspart, insulin glulisine, insulin lispro), intermediate acting insulin (e.g., insulin isophane), long-acting insulin (e.g., insulin degludec, insulin detemir, insulin glargine), amylinomimetic drugs (e.g., pramlintide), alpha-glucosidase inhibitors (e.g., acarbose, miglitol), biguanides (e.g., metformin), dopamine agonist (e.g., bromocriptine), DPP-4 inhibitors (e.g., alogliptin, linagliptin, saxagliptin, sitagliptin), glucagon-like peptides (e.g., albiglutide, dulaglutide, exenatide, liraglutide), meglitinides (e.g., nateglinide, repaglinide), sodium glucose transporter 2 inhibitors (e.g., dapagliflozin, canagliflozin, empagliflozin), sulfonylureas (e.g., glimerpiride, gliclazide, glipizide, glyburide, chlorpropamide, tolazamide, tolbutamide), thiazolidinediones (e.g., rosiglitazone, pioglitazone), or any combination thereof.

Examples of neurological and neurodegenerative disorder treating agents include opioid addiction (e.g., methadone, buprenorphine, naltrexone), nicotine addiction (e.g., bupropion, varenicline), alcohol addiction (e.g., naltrexone, acamprosate, disulfiram), cholinesterase inhibitors (e.g., donepezil, rivastigmine, galantamide), N-methyl-D-aspartate (NMDA) antagonists (e.g., memantine), dietary supplements (e.g., caprylidene), glutamate level reducers (e.g., riluzole), L-DOPA drugs (e.g., levodopa, carbidopa, benserazide, tolcapone, entacapone), dopamine agonists (e.g., bromocriptine, pergolide, pramipexole, ropinirole, piribedil, cabergoline, apomorphine and lisuride), MAO-B inhibitors (e.g., safinamide, selegiline, rasagiline), or any combination thereof.

Examples of cardiovascular disease and blood disorder treating agents include antiplatelets (e.g., aspirin, clopidogrel, prasugrel, ticagrelor), angiotensin-converting enzyme inhibitors (e.g., benazepril, captpril, enalapril, fosinopril, lisinopril, perindopril, quinapril, ramipril, trandolapril), beta-blockers (e.g., acebutolol, atenolol, carvedilol, labetalol, metoprolol, nadolol, nebivolol, penbutolol, pindolol, propranolol), anticoagulants (e.g., warfarin, acenocoumarol, phenprocoumon, dabigatran, apixaban, edoxaban, rivaroxaban), clotting drugs (e.g., Factor VIII, advate, tranexamic acid, desmopressin), hydroxyurea (e.g., droxia, hydrea), antibiotics (e.g., penicillin), statins (e.g., atorvastatin, fluvastatin, lovastatin, pravastatin, rosuvastatin, simvastatin, pitavastatin), vasodilators (e.g., nitric oxide, doxazosin, prazosin, terazosin, clonidine, hydralazine, minoxidil), or any combination thereof.

The following examples further illustrate the invention but, of course, should not be construed as in any way limiting its scope.

Example 1

This example demonstrates the development of small-molecule PRMT5 inhibitors in an embodiment of the invention.

In order to identify PRMT5 inhibitors, the AlphaLISA technique (PerkinElmer, Waltham, Mass.) was adapted to an assay that could precisely quantify PRMT5 dimethylation of its substrate in a 384-well HTS platform (FIG. 1). The AlphaLISA high-throughput screen comprises incubating a biotinylated substrate (e.g., histone H4), PRMT5, and a methyl donor (e.g., S-adenosyl-1-methionine (SAM)); PRMT5 dimethylates the biotinylated substrate and the dimethylated biotinylated substrate is recognized by Acceptor beads specific for the methylation site. Donor beads comprising a tag (e.g., streptavadin) bind to the biotinylated substrate, and interaction between the Acceptor beads and Donor beads emits a signal (e.g., chemiluminescent signal), which can be detected. The methylation activity of PRMT5 is proportional to the intensity of the signal.

In one embodiment of the method used to identify the compounds disclosed herein, PRMT5 enzyme was purified with anti-Flag-M2 beads (Sigma-Aldrich, St. Louis, Mo.) from 293 cells overexpressing the Flag-PRMT5 protein (Wei et al., *Proc Natl Acad Sci USA*, 2013; 110: 13516-13521). The enzyme prep was diluted at 1:10 in assay buffer (30 mM Tris, pH 8.0, 1 mM DTT, 0.01% BSA, 0.01% Tween-20) before use. 100 µM S-adenosylmethionine (SAM) (New England Biolabs, Ipswich, Mass.) was used as the methyl group donor and 30 nM unmethylated histone H4R3 (Anaspec, Thornleigh, Australia) was used as a substrate. For screening, 250 nL of 1 mM library compounds was added to each well with a final compound concentration at 12.5 µM in 1.25% of dimethylsulfoxide (DMSO). All these components were incubated at RT for 1 h. Acceptor beads and donor beads were diluted 1:50 fold in 1× Epigenetics buffer (PerkinElmer, Waltham, Mass.) before use. Acceptor beads were then added at a final concentration of 20 µg/ml to the reaction mixture and the plate was incubated at room temperature (RT) for 1 hour. Donor beads were added at a final concentration of 20 µg/ml, and the plate was incubated at RT for 30 min. The reaction was run in 384 well plates. The plates were read using an ENVISION™ Reader (PerkinElmer, Waltham, Mass.).

A library of 10,000 small molecules was screened, and several potential compounds were identified to significantly inhibit PRMT5 methylation activity. The PRMT5 inhibitory activity of the compounds from the screen was confirmed using both AlphaLISA and an MTT [(3-(4,5-dimethylthiazolyl-2)-2,5-diphenyltetrazolium bromide)] assay (PerkinElmer, Waltham, Mass.). For the MTT assay, cells were seeded at 90% confluence in 96-well plates and titrated with different dosages of compound (IIa) for 4 days. Media was then removed and 100 µl of MTT (Sigma-Aldrich, St. Louis, Mo.) was added per well. Cells were incubated for 2 hours at 37° C. before adding 100 µl of DMSO to each well and quantified with the SYNERGY™ H1 Multi-Mode Reader (BioTek Instruments Inc., Winooski, Vt.).

Amongst the hits, the leading compounds were a compound of formula (II), specifically compound (IIa), a compound of formula (III), specifically compound (IIIa), and a compound of formula (IV), specifically compound (Iva). The $IC_{50}$ of compound (IIa) was ~7.5 µM, the $IC_{50}$ of compound (IIIa) was ~1.5 µM, and the $IC_{50}$ of compound (IVa) was ~16.5 µM, as determined by the AlphaLISA (PerkinElmer, Waltham, Mass.) approach in vitro (FIGS. 2A-2C). To determine whether compound (IIa) reduced p65 methylation of NF-κB, Flag-p65 expressing cells were treated with 20 µM compound (IIa) for 24 hours, Flag-p65 was then pulled down with anti-Flag-M2 beads and analyzed with Western blot by probing with anti-dimethylated arginine (FIG. 2B). Compared to the untreated control, treatment with compound (IIa) significantly inhibited PRMT5-mediated p65 methylation. Additionally, compound (IIa) did not inhibit or had at least a 10-fold higher $IC_{50}$ against other protein arginine methyltransferase family members when analyzed using the HotSpot radioisotope-based platform (Reaction Biology Corp, Malvern, Pa.) (Horiuchi et al., *Assay Drug Dev. Technol.*, 2013; 11: 227-236).

These results indicate that a compound of formula (II), a compound of formula (III), and a compound of formula (IV) can selectively inhibit the activity of PRMT5.

Example 2

This example describes the lead optimization of compound (IIa) to identify small-molecule PRMT5 inhibitors with increased PRMT5 inhibitory activity compared to compound (IIa).

In order to identify small-molecule PRMT5 inhibitors with increased efficacy compared to compound (IIa), lead optimization of compound (IIa) was performed. Briefly, the pyrozolo-pyrimidine core was maintained and peripheral groups were either added or modified. Compounds were tested to identify PRMT5 inhibitors and their corresponding $IC_{50}$ values using an MTT assay. For the MTT assay cells (HT-29 or PANC1) were seeded at 90% confluence in 96-well plates and titrated with different dosages of compound (IIa) for 4 days. Media was then removed and 100 µl of MTT (Sigma-Aldrich) was added per well. Cells were incubated for 2 hours at 37° C. before adding 100 µl of DMSO to each well and quantified with the Synergy H1 Multi-Mode Reader (BioTek Instruments Inc., Winooski, Vt.).

Amongst the compounds, the $IC_{50}$ of compound (Ia) was 2 µM in HT-29 and PANC1 cells, the $IC_{50}$ of compound (If) was 7 µM in HT-29 and 8 µM in PANC1 cells, the $IC_{50}$ of compound (Ig) was 7 µM in HT-29 and 11 µM in PANC1 cells, and the $IC_{50}$ of compound (Ib) was 11 µM in PANC1 cells (FIGS. 3A and 3B).

These results indicate that compounds of formula (I) can selectively inhibit the activity of PRMT5.

Example 3

This example demonstrates that PRMT5 expression is increased in multiple types of cancer.

The expression of PRMT5 was examined in pancreatic ductal adenocarcinoma cells at multiple stages of disease progression and in multiple colorectal cancer cell lines. Pancreatic control (HPNE) and cancer cell lines (PANC1, MiaPaCa2 and AsPC1) were grown in Dulbecco's Modified Eagle Medium (DMEM) (GE Healthcare, Little Chalfont, UK), supplemented with 1% of penicillin/streptomycin, 10% fetal bovine serum (FBS). Colon control (FHC) and cancer (HT29, HCT116, and DLD1) cell lines were maintained in RPMI 1640 Medium (Roswell Park Memorial Institute Medium) (GE Healthcare, Little Chalfont, UK), containing 1% penicillin/streptomycin and 10% FBS, while FHC cells were cultured under the same condition with further addition of 25 mM HEPES (4-(2-hydroxyethyl)-1-piperazineethanesulfonic acid), 10 ng/ml cholera toxin, 0.005 mg/ml insulin, 0.005 mg/ml transferring, and 100 ng/ml hydrocortisone. All cell lines were cultured at 37° C. under 5% $CO_2$.

The expression of PRMT5 in the cell lines was determined by Western blotting using an anti-PRMT5 specific antibody. As shown in FIGS. 4A and 4C, expression of PRMT5 was markedly increased in each of the cell lines tested as compared to the corresponding control cell lines.

The expression of PRMT5 was also analyzed in tissue microarray samples using immunohistochemistry. Pancreatic and colon cancer tissue microarrays with matched normal adjacent controls were acquired from OriGene Technologies (Rockville, Md.). The tissue microarrays were blocked using protein-blocking solution (Dako Corporation, Carpinteria, Calif.) for 30 min. All subsequent staining steps were performed using the Dako FLEX SYSTEM and an automated immunostainer. Incubations were carried out at room temperature and tris buffered saline containing 0.05% TWEEN™ 20, pH 7.4 (Dako Corporation, Carpinteria, Calif.) was used for all the washes and diluents. Anti-PRMT5 primary antibody (Abcam, Cambridge, UK) was used to detect PRMT5 localization. Horseradish peroxidase conjugated to a secondary antibody was then used, followed by addition of the chromogen, which formed a brown precipitate at the binding site of secondary antibody. Imaging was done using an Aperio whole slide digital imaging system (Leica Biosystems, Buffalo Grove, Ill.). The system imaged all slides at 20× magnification.

The expression of PRMT5 was significantly higher in various stages of PDAC (FIG. 4B), particularly in the metastatic stage, as compared to the normal PDAC adjacent pancreatic tissue. Similarly, PRMT5 had much higher expression in samples ranging from inflammation, poylp, to the metastatic stage of CRC as compared to CRC adjacent normal colon tissue (FIG. 4D).

Therefore, these results indicate that the expression of PRMT5 is increased compared to controls in multiple cancer cell types.

Example 4

This example demonstrates that PRMT5 promotes cell proliferation, anchorage-independent growth, and cell migration is cells with increased PRMT5 expression.

The effect of PRMT5 on various characteristics of cancer cells, including cell proliferation, anchorage-independent growth, as well as, cell migration was examined. First, stable cell lines were generated, with either PRMT5 overexpression or shRNA knockdown of PRMT5 in PANC1 (PDAC) and HT29 (CRC) cell lines. Western blotting was carried out to verify the stable overexpression or knockdown of PRMT5 in these cell lines. As shown in FIG. 5A, the stable cell lines showed desired expression level of PRMT5, as expected. Using the above cell models, the effect of PRMT5 on cell growth was determined. As shown in FIGS. 5C and 5D, overexpression of PRMT5 led to a significant increase in the cell growth, while knockdown of PRMT5 showed opposite effect in both PDAC and HT29 derived stable lines, strongly suggesting that PRMT5 is a promoter for cell proliferation.

The ability to form colonies suspended in soft agar is a characteristic of cancer cells. By using the stable cell lines established above, an anchorage-independent assay in soft agar was conducted. 2.5% and 1.25% agar were used to prepare the bottom and top layers of the soft agar, respectively. The bottom agar was added to each well of a 6-well plate. $2 \times 10^5$ cells for each cell line were then added and mixed into top agar solution and layered on top of the bottom layer. The plates were incubated for 10-20 days at 37° C. and 5% $CO_2$. Images were captured using a Canon EOS Rebel T3i Digital SLR camera (Canon, Woodridge, Ill.) and quantification of colony size and number was performed using Image." PRMT5 overexpression led to a significant increase in not only colony size but also colony number, while shPRMT5 knockdown showed the opposite effect in both PANC1 (FIG. 5D) and HT29 (FIG. 5E) cells. This result confirmed that PRMT5 played a critical role in promoting anchorage-independent cell growth in cells with increased PRMT5 expression.

Another important common feature for cancers is the ability for metastasis. Cancer cells often have a stronger migration ability than normal cells, which is critical for tumor invasion and metastases (Shaw, *Methods Mol Biol*, 2005; 294: 97-105). Boyden chamber assays were conducted to determine the effect of PRMT5 on the invasive nature of cells with increased PRMT5 activity. 8 μm pore size cell culture inserts (Corning Inc., Corning, N.Y.) were placed in a 24 well plate. Each chamber was coated with gelatin on the side facing the lower chamber. $2 \times 10^5$ cells were suspended in serum-starved media in the upper chamber of the well. Corresponding serum rich media was added to the lower chamber. Migrated cells were fixed using 4% formaldehyde followed by crystal violet staining and counting using a microscope at 20× magnification. The images were captured using a Canon EOS Rebel T3i Digital SLR camera (Canon, Woodridge, Ill.). As observed in FIG. 5F, overexpression of PRMT5 resulted in an increase in the number of cells that have been migrated, whereas shPRMT5 knockdown reduced this ability as compared to the control cells. Similar effects in CRC cell lines, as shown in FIG. 5G, were also observed. These results pointed out the important role that PRMT5 plays in cell migration.

Taken together, these data show that increased expression of PRMT5 can lead to tumor activity.

Example 5

This example demonstrates the in vitro and in vivo efficacies of a compound of formula (I).

The PDAC and CRC cell lines described above were treated with increasing concentrations of compound (Ia) and quantified for cell viability using the MTT assay described above. As shown in FIGS. 6A and 6B and summarized in FIG. 6C, compound (Ia) had an $IC_{50}$ of 4.3 μM in PDAC cells (PANC1), and an $IC_{50}$ of 2.2 μM in CRC cells (HT29).

Experiments were also conducted to determine whether compound (Ia) exhibits tumor inhibition effects in mice xenograft models of cancer with increased PRMT5 activity. NSG (NOD scid gamma) mice were obtained from the In Vivo Therapeutics Core at Indiana University School of Medicine. After acclimation for 7 days, NSG mice (6-8 weeks old) were xenografted with mycoplasma-free PANC1 or HT29 cells subcutaneously ($1\times10^7$ PANC1 or $3\times10^6$ HT29 cells used per mouse in 0.2 ml of a 1:1 mix of phosphate-buffered saline and MATRIGEL™) (BD Biosciences, San Jose, Calif.). Mice were randomized when tumor volumes reached about 100 mm³. Mice were treated with either vehicle control or 20 mg/kg of compound (Ia) (drug stock dissolved in 1:1 CREMOPHOR™:ethanol solution) intraperitoneally 3 times per week. Tumor volumes and body weights were measured twice a week. The study was performed in accordance with the guidelines and standards of the Institutional Animal Care and Use Committee (IACUC). As shown in FIGS. 7A and 7B, injection of compound (Ia) did not visibly affect the body weight of the implanted mice, however, it led to significant tumor inhibition effect in both PANC1 (FIG. 7C) and HT29 (FIG. 7D) xenografted mice, demonstrating the strong anti-tumor efficacy of compound (Ia) against PRMT5 expressing cancers.

Example 6

This example demonstrates the in vitro and in vivo efficacies of a compound of formula (II).

The PDAC and CRC cell lines described above were treated with increasing concentrations of compound (IIa) or the commercially available PRMT5 inhibitor EPZ015666

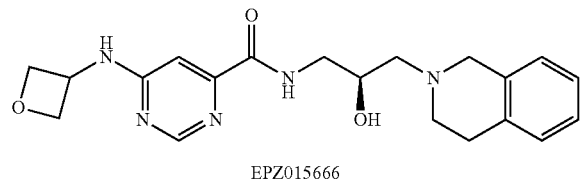 [SMILES: O=C(NC[C@H](O)CN1CCc2ccccc2C1)c1cc(NC2COC2)ncn1]

EPZ015666 and quantified for cell viability using the MTT assay described above. As shown in FIGS. 8A to 8F and summarized in FIG. 8G, compound (IIa) had a range of $IC_{50}$ at 2-4 μM in PDAC cells (PANC1, MiaPaCa2 and AsPC1), and a range of $IC_{50}$ at 10-11 μM in CRC cells (HT29, HCT116 and DLD1). A soft agar experiment was also performed to determine the effect of compound (IIa) on colony growth. As indicated in FIG. 8H, treatment with compound (IIa) strongly inhibited colony formation of both PDAC and CRC cells.

The commercially available PRMT5 inhibitor, EPZ015666, was much less effective as compared to compound (IIa), with a range of $IC_{50}$ at 50-95 μM for PDAC cells, and a range of $IC_{50}$ at 180-195 μM for CRC cells (FIGS. 9A-9F).

Experiments were also conducted to determine whether compound (IIa) exhibits tumor inhibition effects in mice xenograft models of cancer with increased PRMT5 activity. NSG (NOD scid gamma) mice were obtained from the In Vivo Therapeutics Core at Indiana University School of Medicine. After acclimation for 7 days, NSG mice (6-8 weeks old) were xenografted with *mycoplasma*-free PANC1 or HT29 cells subcutaneously ($1\times10^7$ PANC1 or $3\times10^6$ HT29 cells used per mouse in 0.2 ml of a 1:1 mix of phosphate-buffered saline and MATRIGEL™) (BD Biosciences, San Jose, Calif.). Mice were randomized when tumor volumes reached about 100 mm³. Mice were treated with either vehicle control or 20 mg/kg of compound (IIa) (drug stock dissolved in 1:1 CREMOPHOR™:ethanol solution) intraperitoneally 3 times per week. Tumor volumes and body weights were measured twice a week. The study was performed in accordance with the guidelines and standards of the Institutional Animal Care and Use Committee (IACUC). As shown in FIGS. 10A and 10B, injection of compound (IIa) did not visibly affect the body weight of the implanted mice, however, it led to significant tumor inhibition effect in both PANC1 (FIG. 10C) and HT29 (FIG. 10D) xenografted mice, demonstrating the strong anti-tumor efficacy of compound (IIa) against PRMT5 expressing cancers.

Example 6

This example demonstrates that a PRMT5 inhibitor of formula (II) inhibits NF-κB activation and its target gene expression in cells with increased expression of PRMT5.

Previously, it was discovered that PRMT5 activates NF-κB through methylation of its p65 subunit in HEK293 cells (Wei et al., *Proc Natl Acad Sci USA*, 2013; 110: 13516-13521; Wei et al., *Cell Cycle*, 2013; 13: 32-41). As shown in FIGS. 11A and 11B, overexpresion of PRMT5 enhances NF-κB activity, while PRMT5 knockdown causes the opposite effect in both PANC1 (FIG. 11A) and HT-29 (FIG. 11B) cells. To determine if compound (IIa) decreases NF-κB activity, cells transfected with a NF-κB luciferase construct were treated with increasing concentrations of compound (IIa) or the control compound EPZ015666. As shown in FIGS. 11C and 11D, treatment with increasing concentrations of compound (IIa) resulted in a corresponding decrease in NF-κB activation in PANC1 (FIG. 11C) as well as HT29 cells (FIG. 11D). In great contrast, a much higher concentration of EPZ015666 was required to observe the same effect (FIGS. 11C and 11D). These results demonstrate the high efficacy of compound (IIa) to decrease the NF-κB activation in PDAC as well as CRC cells.

The effect of overexpression of PRMT5 on downstream targets of NF-κB was also analyzed. As shown in FIGS. 11E-11H, overexpression of PRMT5 significantly enhanced IL-1β-triggered typical NF-κB target genes expression, TNFα and IL8, while shPRMT5 exhibited the opposite effect, in both PANC1 (FIGS. 11E and 11F) and HT29 cells (FIGS. 11G-11H).

Furthermore, experiments were performed to determine if PRMT5 inhibition by compound (IIa) could decrease the expression of NF-κB target genes (e.g., pro-inflammatory cytokines TNFα and IL-8). Briefly, HT29 and PANC1 cells were treated with or without compound (IIa), and target gene expression was analyzed by quantitative PCR. Treatment with compound (IIa) led to a significant decrease in the expression of TNFα and IL8 in both PANC1 (FIGS. 11I-11J) and HT29 cells (FIGS. 11K-11L), thus indicating that compound (IIa) decreased the PRMT5-mediated NF-κB-dependent gene activation. Overall, compound (IIa) showed significant efficacy in targeted reduction of NF-κB activation as well as its downstream gene activation in both PDAC and CRC cells.

Therefore, taken together, these data show that the PRMT5 inhibitors disclosed herein can reduce that activity of NF-κB and subsequently reduce the expression of NF-κB target genes. Additionally, these data demonstrate that compound (IIa) can be used to treat inflammatory and autoimmune diseases via the inhibition of TNF and IL-8.

Example 7

This example demonstrates the efficacy of a compound of formula (III) and a compound of formula (IV).

The PDAC and CRC cell lines described above were treated with increasing concentrations of compound (IIIa) or compound (IVa) and quantified for cell viability using the MTT assay described above. As shown in FIGS. 12A to 12L and summarized in FIG. 12M, compound (IIIa) had a range of $IC_{50}$ at 8.5-12.5 μM in PDAC cells (PANC1, MiaPaCa2 and AsPC1), and a range of $IC_{50}$ at 5-11 μM in CRC cells (HT29, HCT116 and DLD1), and compound (IVa) had a range of $IC_{50}$ at 22-51 μM in PDAC cells (PANC1, MiaPaCa2 and AsPC1), and a range of $IC_{50}$ at 35-50 μM in CRC cells (HT29, HCT116 and DLD1).

These results demonstrate the strong anti-tumor efficacy of a compound of formula (III) and a compound of formula (IV) against PRMT5 expressing cancers.

Example 8

This example demonstrates that PRMT5 activity is increased in neurological and neurodegenerative disorders.

The expression of PRMT5 was analyzed by Western blot is samples from models of Alzheimer's disease. Briefly, samples were taken from non-transgenic B6 mice (6M) (control), hTau (humanized tau mice) (3M), hTau (6M), htau; Trem2-/- mice (6M), hTau (18M), and APPPS1 amyloid mice. Cells overexpressing PRMT5 were also used as a control. From these data, APPPS1 mice showed a significant increase in PRMT5 protein expression compared to age-matched B6 control mice (FIGS. 13A and 13B). Additionally, PRMT5 expression is increased along the aging of another Alzheimer's disease mouse model—hTau expression model and hTau/Trem2-/- mouse model.

Taken together, these data show that PRMT5 activity is increased in neurological and neurodegenerative disorders, and indicate that inhibition of PRMT5 with a compound of formula (I), formula (II), formula (III), or formula (IV), or a pharmaceutically acceptable salt thereof can be an effective treatment.

Example 9

This example demonstrates that a compound of formula (II) can be used to treat a neurological disorder.

Methamphetamine induces inflammation and activation of microglia through NFκB. Increased NFκB promotes inflammation and excitotoxicity are associated with neuronal damage and decrease in neurotransmitter (NT) levels of dopamine and serotonin. Thus inhibition of NF-κB via compound (IIa) mediated inhibition of its activator, PRMT5 could reduce neurotoxicity observed during post-meth administration and restore NT levels. This data suggests that compound (IIa) may be used to treat methamphetamine abuse.

Rats were given methamphetamine treatment 7.5 mg/kg, 4 injections spaced out at 2 hours each. Then, 4 injections of 1 mg/kg of compound (IIa) or vehicle control were given at 12 hours, 24 hours, 36 hours, and 48 hours after the last methamphetamine injection. Rats were sacrificed 24 hours after the last injection and neurotransmitter levels were quantified in the striatum using high performance liquid chromatography (HPLC). In the group administered the compound of formula (II), an increase in the levels of NT levels were observed in the striatum region of the rats, thereby suggesting a neuroprotective effect (FIGS. 14A and 14B).

These data show that treatment with a compound of formula (II) can be used for the treatment of neurological disorders. Moreover, these data indicate that compounds of formula (I), formula (III), or formula (IV), or a pharmaceutically acceptable salt thereof may be effective for the treatment of neurological disorders.

Example 10

This example demonstrates that PRMT5 is highly expressed in the heart.

The expression level of PRMT5 was analyzed in multiple tissues using the TiGER database. The expression profile PRMT5 in humans shows a significant expression of PRMT5 in heart tissue (FIG. 15).

These data indicate that inhibition of PRMT5 with a compound of formula (I), formula (II), formula (III), or formula (IV), or a pharmaceutically acceptable salt thereof may be an effective treatment for cardiovascular disease.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound having a structure selected from the group consisting of:

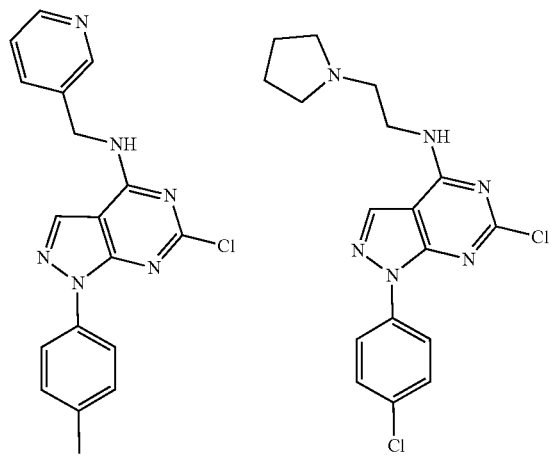

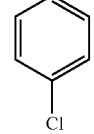

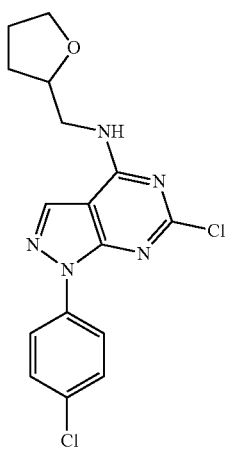

or a pharmaceutically acceptable salt thereof.

2. The compound of claim 1, wherein the compound has the structure:

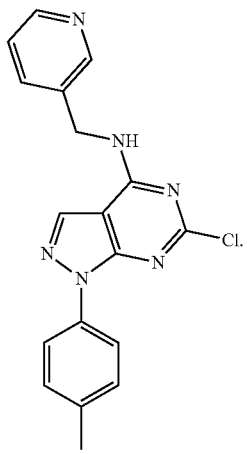 [SMILES: Cc1ccc(-n2ncc3c(NCc4cccnc4)nc(Cl)nc32)cc1]

3. A compound of formula (I):

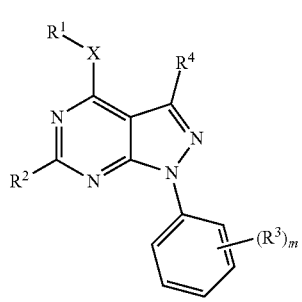

wherein

R¹ is selected from the group consisting of piperazinyl, pyrrolyl, pyrrolidinyl pyranyl, piperidyl, morpholinyl, pyridinyl, and tetrahydrofuranyl;

R² is halo;

R³ is $C_1$-$C_8$ alkyl or halo;

R⁴ is H;

X is —NH(CH$_2$)$_o$—;

o is 1 or 2; and m is 1; or a pharmaceutically acceptable salt thereof.

4. A pharmaceutical composition comprising at least one compound of claim 3 or pharmaceutically acceptable salt thereof and a pharmaceutically acceptable carrier.

5. A method of inhibiting the activity of PRMT5 in a cell, comprising administering a pharmaceutically effective amount of a compound of claim 3 or a pharmaceutically acceptable salt thereof to the cell, whereby the activity of PRMT5 is inhibited.

6. The method of claim 5, wherein (i) the cell is a cancer cell; and/or (ii) the cancer cell is optionally selected from a gastrointestinal cancer, skin cancer, lung cancer, brain cancer, ovarian cancer, prostate cancer, lymphoma, melanoma, or breast cancer; and wherein the gastrointestinal cancer is optionally selected from the group consisting of pancreatic ductal adenocarcinoma (PDAC), colorectal cancer, pancreatic cancer, and liver cancer.

7. A compound having the general formula of:

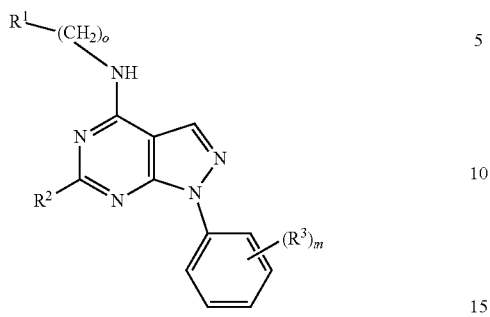

wherein

R¹ is selected from the group consisting of piperazinyl, homopiperazinyl, pyrrolyl, pyrrolinyl, pyrazolyl, pyranyl, piperidyl, morpholinyl, pyridinyl, pyridazinyl, pyrimidyl, and pyrazinyl;

$R^2$ is halo, or —NH(CH$_2$)$_n$NR$^5$R$^6$;

$R^3$ is $C_1$-$C_8$ alkyl, or halo;

$R^5$ and $R^6$ are independently $C_1$-$C_8$ alkyl;

m is 1; n is an integer from 1-5; and o is 1 or 2;

or a pharmaceutically acceptable salt thereof.

* * * * *